(12) United States Patent
Harada et al.

(10) Patent No.: US 6,184,433 B1
(45) Date of Patent: Feb. 6, 2001

(54) PRESSURE-RESISTANT ABSORBENT RESIN, DISPOSABLE DIAPER USING THE RESIN, AND ABSORBENT RESIN, AND METHOD FOR PRODUCTION THEREOF

(75) Inventors: Nobuyuki Harada; Kunihiko Ishizaki, both of Osaka; Hirotama Fujimaru; Toshimasa Kitayama, both of Hyogo, all of (JP)

(73) Assignee: Nippon Shokubai Co., Ltd., Osaka-Fu (JP)

( * ) Notice: Under 35 U.S.C. 154(b), the term of this patent shall be extended for 0 days.

(21) Appl. No.: 09/058,023

(22) Filed: Apr. 10, 1998

(30) Foreign Application Priority Data

Apr. 14, 1997 (JP) ................................................ 9-096067
Jun. 13, 1997 (JP) ................................................ 9-156267

(51) Int. Cl.$^7$ .............................. A61F 13/15; C08J 9/00; C08L 15/00
(52) U.S. Cl. ......................... 604/372; 604/358; 604/367; 604/368; 520/1; 521/50; 523/111
(58) Field of Search .................................. 604/368, 372, 604/367, 358; 521/50; 523/111

(56) References Cited

U.S. PATENT DOCUMENTS

| | | |
|---|---|---|
| 5,145,906 | 9/1992 | Chambers et al. . |
| 5,149,334 * | 9/1992 | Lahrman et al. ..................... 604/367 |
| 5,149,335 | 9/1992 | Kellenberger et al. .............. 604/372 |
| 5,241,009 | 8/1993 | Yarbrough et al. ................ 525/327.8 |
| 5,314,420 | 5/1994 | Smith et al. ......................... 604/358 |
| 5,314,952 | 5/1994 | Choi et al. ........................... 525/119 |
| 5,462,972 | 10/1995 | Smith et al. . |
| 5,486,569 | 1/1996 | Henderson et al. ................. 525/116 |
| 5,506,324 | 4/1996 | Gartner et al. . |
| 5,574,121 * | 11/1996 | Irie et al. ......................... 526/318.44 |
| 5,601,542 | 2/1997 | Melius et al. ........................ 604/368 |
| 5,610,220 | 3/1997 | Kimmek et al. . |
| 5,629,377 | 5/1997 | Burgert et al. ....................... 524/832 |
| 5,684,106 | 11/1997 | Johnson et al. ...................... 526/295 |
| 5,712,316 | 1/1998 | Dahmen et al. ........................ 521/72 |
| 5,760,080 | 6/1998 | Wada et al. . |

FOREIGN PATENT DOCUMENTS

| | | |
|---|---|---|
| 196 30 131 A1 | 3/1997 | (DE) . |
| 0 317 106 A2 | 5/1989 | (EP) . |
| 0339 461 A1 | 11/1989 | (EP) . |
| 0 450 924 A2 | 10/1991 | (EP) . |
| 0 509 708 A1 | 10/1992 | (EP) . |
| 0 532 002 A1 | 3/1993 | (EP) . |
| 0 695 762 A1 | 2/1996 | (EP) . |
| 0744735 * | 11/1996 | (EP) . |
| 0 744 435 A1 | 11/1996 | (EP) . |
| 0 761 241 A2 | 3/1997 | (EP) . |
| 0 811 636 A1 | 12/1997 | (EP) . |
| 0 812 873 A1 | 12/1997 | (EP) . |
| 0 827 753 A2 | 3/1998 | (EP) . |
| 0 837 076 A2 | 4/1998 | (EP) . |
| 2 435 485 | 9/1979 | (FR) . |
| 2 525 121 | 4/1983 | (FR) . |
| 60-135432 | 7/1985 | (JP) . |
| 63-99861 | 2/1988 | (JP) . |
| WO 94/09043 | 4/1994 | (WO) . |
| WO 95/05856 | 3/1995 | (WO) . |
| WO 95/27739 | 10/1995 | (WO) . |
| WO 96/05234 | 2/1996 | (WO) . |

* cited by examiner

*Primary Examiner*—John G. Weiss
*Assistant Examiner*—Miley Craig Peppers
(74) *Attorney, Agent, or Firm*—Fish & Richardson P.C.

(57) ABSTRACT

This invention is directed to a disposable diaper using a pressure-resistant absorbent resin manifesting a ratio of water absorption capacity under pressure of 30 g/g or more to artificial urine under a load of 50 g/cm$^2$, and a pressure-resistant absorption ratio of 0.6 or more, wherein the pressure resistant absorption ratio is defined as the ratio of the ratio of water absorption capacity under high pressure to artificial urine under a load of 100 g/cm$^2$ to a ratio of water absorption capacity under pressure to artificial urine under a load of 50 g/cm$^2$.

26 Claims, 1 Drawing Sheet

PRESSURE-RESISTANT ABSORBENT RESIN, DISPOSABLE DIAPER USING THE RESIN, AND ABSORBENT RESIN, AND METHOD FOR PRODUCTION THEREOF

BACKGROUND OF THE INVENTION

1. Field of the Invention

This invention relates to a disposable diaper excelling in resistance to pressure and an absorbent resin excelling in resistance to pressure. Further, this invention relates to an absorbent resin preeminently excelling in affinity for aqueous liquids and exhibiting prominently improved speed of absorption and ratio of water absorption capacity under no pressure and under pressure as compared with the conventional equivalents and a method for the production thereof.

2. Description of Related Art

In recent years, absorbent resins capable of absorbing some ten to some hundred times their own weights of water have been developed and have been found utility in various applications requiring absorption and retention of water such as in the field of hygienic materials including sanitary goods and disposable diapers, the field of agriculture and horticulture, the field of foodstuffs requiring retention of freshness, and the field of industrial products requiring protection against dew formation and refrigeration.

The absorbent resins of this class have been known in various types such as, for example, a hydrolyzed starch-acrylonitrile graft polymer, neutralized starch-acrylic acid graft polymer, saponified vinyl acetate-acrylic ester copolymer, hydrolyzed acrylonitrile copolymer or the product of cross-linkage thereof, hydrolyzed acrylamide copolymer or the product of cross-linkage thereof, self-cross-linking polyacrylic acid salts, and partially neutralizing cross-linked polyacrylic acid salts.

The absorbent resin has the necessary quality thereof varied by the kind of use. As the characteristics which are required by an absorbent resin intended for such hygienic materials as disposable diaper, for example, high ratio of water absorption capacity, high speed of absorption, large capacity for permeation, etc. to be manifested to an aqueous liquid under pressure may be cited. EP 443627, for example, discloses an absorbent structure which uses an absorbent resin excelling in ratio of water absorption capacity and speed of absorption under pressure in a concentration of not less than 60 wt %. The properties of ratio of water absorption capacity and speed of absorption do not always exhibit a positive correlation. Particularly, the ratio of water absorption capacity and the speed of absorption under pressure betray antinomy. It is, therefore, difficult to have these two properties simultaneously improved.

Addition to surface area, for example, has been tried with a view to enabling an absorbent resin to acquire a heightened speed of absorption. Attempts have been made to decrease the particle diameter of the absorbent resin or fabricate the absorbent resin in the form of granules or scales. Generally when the absorbent resin is given a decreased particle diameter with a view to adding to surface area, however, the absorbent resin conversely suffers a decrease in the ratio of water absorption capacity under pressure or under no pressure because the decrease of particle diameter degrades the physical strengths of resin and contracts the gaps between the particles of resin swelled with absorbed water.

A technique is known which cross-links molecular chains near the surface of an absorbent resin and increases the cross-link density in the surface layer of the resin with a view to enabling the polymer, when swelled with absorbed water, to secure gaps for transfer of liquid between the particles thereof and consequently prevent the absorbent resin from decreasing the ratio of water absorption capacity even on exposure to pressure. Incidentally, the largeness of surface area and the ratio of water absorption capacity under pressure generally contradict each other such that the surface layer of resin is cross-linked uniformly based on difficulty of uniformity mixing of the resin and a cross-linking agent when the particles of resin have an increased surface area. Most of the improvements achieved to date with a view to heightening the ratio of water absorption capacity of an absorbent resin under pressure and increasing the speed of absorption thereof as well have stemmed from combinations of the two methods (increase of surface area and cross-linkage near surface) mentioned above. Regretfully, however, these improvements are incapable of yielding satisfactory results owing to the technical limit imposed by the fact that the two properties contradict each other as mentioned above.

As a means for breaking through this technical limit by enlarging the surface area without decreasing the particle diameter, the concept of obtaining a porous polymer by using a foaming agent and so on and the technique for giving a cross-linking treatment to the proximity of the surface of the polymer have been proposed in recent years. As concrete examples of this approach, a method which comprises polymerizing a 70 mol % neutralized aqueous sodium polyacrylate solution in the presence of a cross-linking agent and a carbonate as a foaming agent and cross-linking the proximity of the surface of the produced polymer (U.S. Pat. No. 5,314,420 and JP-A-07-185331), a method which comprises polymerizing a 70 mol % neutralized aqueous potassium polyacrylate or aqueous ammonium salt solution in the presence of a cross-linking agent and a carbonate salt as a foaming agent and a cross-linking the proximity of the surface of the produced polymer (WO 9502002, U.S. Pat. No. 5,712,316 and EP 707603), a method which comprises polymerizing a partially neutralized aqueous sodium acrylate solution in the presence of a solid foaming agent in a dispersed state and giving a cross-linking treatment to the proximity of the surface of the produced polymer (EP 744435), and besides a method using foaming agents a method which comprises obtaining a sodium acrylate polymer with a porous surface by the reverse-phase suspension polymerization performed in the presence of a specific surfactant and giving a cross-linking treatment to the proximity of the surface of the polymer (EP 0695762) may be cited.

Indeed, these methods which give a cross-linking treatment to the proximity of the surface of a porous polymer using a foaming agent have improved the ratio of water absorption capacity and the speed of absorption under pressure. In spite of the improvements, however, these methods still suffer degradation of the affinity of the surface of the polymer, typically porous in texture, for water because the porous polymer, on being subjected to the cross-linking treatment given to the proximity of the surface thereof, does not permit each control of the cross-link density owing to the polymer constitution itself the absorbent resin when the density of cross link in the surface is increased for the purpose of heightening the ratio of water absorption capacity under pressure. In spite of deliberate use of the porous polymer, therefore, there are problems of ultimate degradation of the speed of absorption.

It has been heretofore known to use such absorbent resin as exhibits a high ratio of water absorption capacity under pressure under load for disposable diapers. The loads proposed to date for use in the determination of a ratio of water absorption capacity, a factor typically representing physical properties fit for actual use of a relevant absorbent resin in diapers include 10 g/cm² (JP-A-60-135432), 0.3 psi (about 20 g/cm², EP 0339461), 50 g/cm² (JP-A-63-99861), 63000 dynes/cm² (about 50 g/cm², WO 9511932, U.S. Pat. No. 5,684,106),60 g/cm² (EP 707603), total of minimum 0.01 —maximum of 0.7 psi (total of about 0.7 g/cm²—maximum of 63 g/cm², U.S. Pat. No. 5,601,542), and 0.6 through 1 psi (about 43 g/cm² through about 71 g/cm², JP-A-08-510484, U.S. Pat. No. 5,629,377), for example. The absorbent resins which reflect these specific loads have been disclosed there. Among these conventional absorbent resins, those which exhibit the highest ratios of water absorption capacity under pressure are the absorbent resin manifesting a ratio of 25.9 g/g under a load of 1 psi (about 71 g/cm²) (Test Run 6e of JP-A- 09-501975, WO 9505856) and the absorbent resin manifesting a ratio of 8 ml/g under a load of 1.7 psi (about 121 g/cm²) (Table B of EP 0339461). While these absorbent resins manifest ratios of water absorption exceeding 30 g/g under relatively low pressure, these ratios of water absorption capacity under load notably fall generally as the load increases (U.S. Pat. No. 5,601,542, EP 0707603, U.S. Pat. No. 5,629,377, and Table B of EP 0339461). When the load increases from 0.3 psi to 0.6 psi, for example, the ratio of water absorption capacity under pressure in most cases falls notably to not more than one half. The resins under a load of 100 g/cm² (about 1.4 psi) manifested a capacity for absorption of not more than 10 g/g, or not more than 20 g/g at most, even when the surface area of resin was increased for getting preeminently speed of absorption. Regretfully, the conventional techniques have not fully satisfied the needs of the market for an absorbent resin manifesting high ratio of water absorption capacity under pressure and fair speed of absorption under still higher pressure, i.e. conditions necessary for a disposable diaper of high performance. Thus, an absorbent resin which satisfactorily reconciles the two factors, i.e. ratio of water absorption capacity and speed of absorption, remains yet to be completed.

In the case of a disposable diaper, since a baby wearing one incessantly moves about and, therefore, exerts unsteady load thereon, there are times when even an absorbent resin manifesting a due ratio of water absorption capacity under high pressure fails to exhibit a stable capacity for absorption to pressure. Simply because an absorbent resin manifests a due ratio of water absorption capacity under a load of 10 to some tens of g/cm² which is estimated from the standard body weight (about 10 kg) of a baby, when incorporated in an actual diaper, is suspected that the absorbent resin fails to bring about a fully satisfactory result in disposable diapers. When the ratio of water absorption capacity under pressure which has been determined by simply varying the load (10—some tens of g/cm²) as practiced heretofore is relied on to rate or screen a given absorbent resin, it does not serve as a reliable index for the performance of the absorbent resin such as in disposable diapers. For the purpose of final evaluation of an absorbent resin intended for use in a diaper, the determination of the absorbent resin for such physical properties as ratio of water absorption capacity under pressure is not satisfactory. As things now stand, it is after all necessary to spend cost, time, and labor copiously to manufacture diapers and subject them to a test by monitors.

SUMMARY OF THE INVENTION

It is an object of this invention is to provide an absorbent resin which enjoys heretofore unattainable excellent absorption properties perfectly reconciling the two factors, ratio of water absorption capacity and speed of absorption under pressure, at a very high level approximating the known technical boundaries.

A further object of this invention is to provide a method for the production of an absorbent resin which manifests a high ratio of water absorption capacity under no pressure and under pressure and a high speed of absorption under no pressure and under pressure.

Still another object of this invention is to provide a pressure-resistant absorbent resin which manifests such a high ratio of water absorption capacity as has never been attained by any conventional absorbent resin under high pressure of 100 g/cm², incurs a decline of the ratio of water absorption capacity only sparingly owing to addition to the pressure, and manifests a fully satisfactory ratio of water absorption capacity.

Yet another object of this invention is to provide a disposable diaper which uses the pressure-resistant absorbent resin mentioned above and, therefore, manifests a high ratio of water absorption capacity even when a baby wearing this diaper moves about and exerts incessantly varying load thereon, suffers leakage of urine only sparingly, and offers a large capacity for absorption.

The invention has a further object of providing an absorbent resin which manifests a high ratio of water absorption capacity under pressure in spite of a large surface area of the particles thereof.

Besides, it is an object of this invention to provide a parameter for an absorbent resin which is correlated with the actual use of a diaper in the determination of physical properties of the absorbent resin.

The objects mentioned above are accomplished by the following items (1)–(6).

(1) An absorbent resin produced by adding a compound having a plurality of functional groups capable of reacting with a group represented by formula —COOR in which each R is independently hydrogen atoms, metal atoms or ammonium to an absorbent cross-linked polymer having a —COOR group of 12 mmol/g or more and a molecular ratio of —COOH/—COOR of not more than 0.5.

(2) An absorbent resin having the proximity of the surface thereof subjected to a cross-linking treatment with a compound having a plurality of functional groups capable of reacting with a group represented by formula —COOR in which each R is independently hydrogen atoms, metal atoms or ammonium, having a —COOR group in a concentration of 12 mmol/g or more and a molecular ratio of —COOH/— COOR of not more than 0.5.

(3) An absorbent resin having a BET specific surface area of 0.03 m²/g or more and a ratio of water absorption capacity under high pressure of 25 g/g or more to artificial urine under a load of 100 g/cm².

(4) A pressure-resistant absorbent resin manifesting a ratio of water absorption capacity under pressure of 30 g/g or more to artificial urine under a load of 50 g/cm², and a pressure-resistant absorption ratio of 0.6 or more, wherein said pressure-resistant absorption ratio is defined as the ratio of said ratio of water absorption capacity under high pressure to artificial urine under a load of 100 g/cm² to a ratio of water absorption capacity under pressure to artificial urine under a load of 50 g/cm².

(5) A disposable diaper using a pressure-resistant absorbent resin manifesting a ratio of water absorption capacity under pressure of 30 g/g or more to artificial urine under a load of 50 g/cm$^2$, and a pressure-resistant absorption ratio of 0.6 or more, wherein said pressure-resistant absorption ratio is defined as the ratio of said ratio of water absorption capacity under high pressure to artificial urine under a load of 100 g/cm$^2$ to a ratio of water absorption capacity under pressure to artificial urine under a load of 50 g/cm$^2$.

(6) A method for the production of an absorbent resin, characterized by adding a compound having a plurality of functional groups capable of reacting with a group represented by formula —COOR in which each R is independently hydrogen atoms, metal atoms or ammonium to an absorbent cross-linked polymer having a —COOR group of 12 mmol/g or more and a molecular ratio of —COOH/—COOR of not more than 0.5 and heating the resultant mixture.

Surprisingly, this invention, by using as a base polymer a polymer of improved —COOR density, namely an absorbent cross-linked polymer containing —COOR groups in a concentration of 12 mmol/g or more and having a molecular ratio of —COOH/—COOR of not more than 0.5., allows a notable increase of the speed of absorption without a decrease in the speed of absorption even after the secondary cross-linking treatment performed in the proximity of the surface.

Further, the absorbent cross-linked polymer of improved——COOR density mentioned above allows production of an absorbent resin which shows a notable reduction in the time required for the secondary cross-linking treatment irrespectively of the morphology, namely the choice among such forms as spherical particles, crushed particles, scaly particles, and porous particles and manifests speed of absorption and ratio of water absorption capacity under no pressure or under pressure at fully satisfactorily reconciling levels as compared with those obtained heretofore.

The polymer of improved —COOR density as the base polymer, namely the absorbent cross-linked polymer containing —COOR groups in a concentration of 12 mmol/g or more and having a molecular ratio of —COOH/—COOR of not more than 0.5., is subjected to surface cross-linkage using a covalent cross-linking agent and then the resultant absorbent resin is caused to have the ratio of water absorption capacity thereof under no load lowered to 0.9–0.3 times the level which existed prior to the cross-linkage. Producing these absorbent resin, it is obtained a novel pressure-resistant absorbent resin which manifests such a high ratio of water absorption capacity under pressure as has never been attained by the conventional absorbent resin even under a load of 100 g/cm$^2$ and shows an extremely small decrease in the capacity for absorption in spite of a notable increase of load from 50 g/cm$^2$ to 100 g/cm$^2$, namely a product which possesses a high pressure-resistant absorption ratio and manifests highly satisfactory absorption under load of any level.

Further, use of this pressure-resistant absorbent resin permits production of a disposable diaper which manifests a high ratio of water absorption capacity under pressure, suffers leakage of urine only sparingly, and enjoys a large capacity for absorption even when the load incessantly moves about and varies.

This invention has established that not only the ratio of water absorption capacity under pressure to artificial urine under a load of 50 g/cm$^2$ proposed to date but also the pressure-resistant absorption ratio defined as the ratio of the ratio of water absorption capacity under high pressure to artificial urine under a load of 100 g/m$^2$ to the ratio of water absorption capacity under pressure of 50g/cm$^2$ mentioned below, namely the ratio; (the ratio of water absorption capacity under high pressure to artificial urine under a load of 100 g/cm$^2$) (the ratio of water absorption capacity under pressure to artificial urine under a load of 50 g/cm$^2$), serves as an important index for the acceptability of a given absorbent resin for use in a disposable diaper. That is to say, while it has been known that the ratio of water absorption capacity under pressure is lowered by increasing the load, this invention has established that the stability of the ratio of water absorption capacity under specific levels of pressure (100 g/cm$^2$ and 50 g/cm$^2$) is important for a disposable diaper.

The present invention has perfected for the first time an absorbent resin manifesting such a high ratio of cubical absorption as 23 g/g under high pressure in spite of such a large specific surface area as not less than 0.3 m$^2$/g and has also discovered that this novel absorbent resin is used highly effectively in a disposable diaper. Further, this invention has established that this parameter of the absorbent resin is very satisfactorily correlated with the result of actual use of the disposable diaper (the results of evaluation of disposable diapers by monitors).

Figure 1:
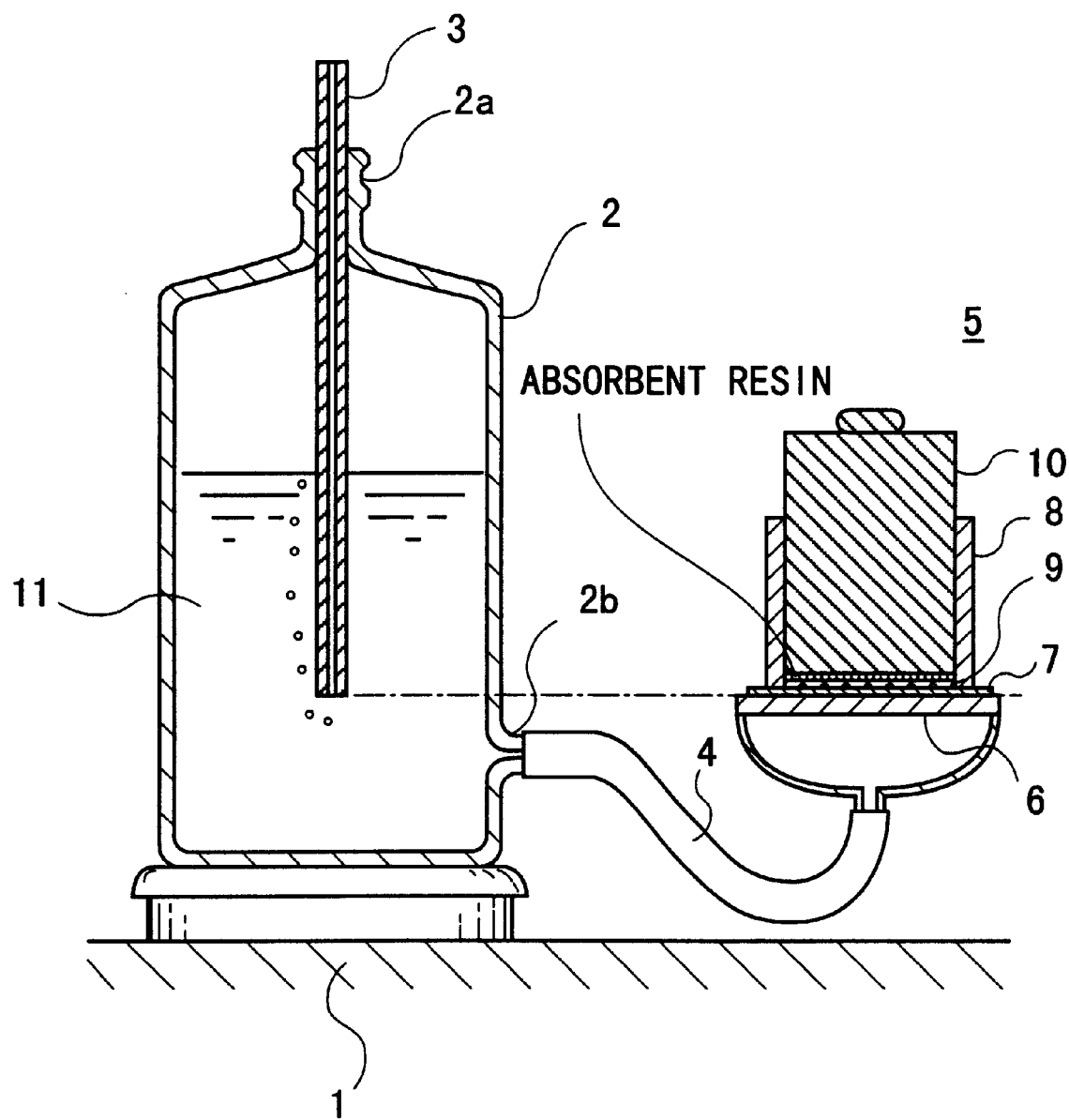
FIG. 1 illustrates a device used in the present invention for the determination of the ratio of water absorption capacity under pressure.

DESCRIPTION OF PREFERRED EMBODIMENT (I) Absorbent cross-linked polymer

An absorbent cross-linked polymer used in the present invention has a group represented by formula —COOR in which each R is independently hydrogen atoms, metal atoms or ammonium and a ratio of —COOH/—COOR of not more than 0.5. Examples of R are alkali metal such as lithium sodium potassium rubidium cesium, alkaliearth metal such as beryllium magnesium calcium, transition element such as zinc and other metal such as aluminum. Example of ammonium contains ammonium(NH$_4$), primary ammonium such as monoethanolammonium, methyammonium, secondary ammonium such as dimethylammonium and dimethylammonium, tertiary ammonium such as triethanolammonium triethylammonium, and quarternary ammonium such as tetramethyammonium. A preferable R is a hydrogen atom, alkali metal or ammonium(NH$_4$), more preferable is a hydrogen atom, lithium, sodium, or ammonium(NH$_4$). R is used in the present invention form of simple kind or a mixture of two or more kinds. This invention has established by the absorbent cross-linked polymer having —COOR group of 12 mmol/g or more for governing factor for the ratio of water absorption capacity and the speed of absorption under pressure. Herein the —COOR group of the absorbent cross-linked polymer contains total of carboxyl group (—COOH) and neutralized thereof per unit amount of the absorbent cross-linked polymer. If the ratio of —COOH/—COOR is 0.5 or more, the shortage will bring about disadvantages such as jeopardizing the stability and degrading various physical properties such as speed of absorption and ratio of water absorption capacity under pressure. If the absorbent cross-linked polymer has a —COOR group content of 12 mmol/g or more, it will not allow production of an absorbent resin which satisfactorily reconcile a ratio of water absorption 10 capacity and a speed of absorption under pressure as well as improved absorbing peculiarity, as aimed at by this invention.

The —COOR density of the absorbent cross-linked polymer can be expressed by the amount of COOR groups per unit amount of the absorbent resin in theoretically. In the case of a polymer (molecular weight of 94 g/mol) produced by polymerization of acrylic acid and neutralizing carboxyl group with sodium hydroxide of 100 mol %, for example, —COOR content is computed in accordance with the following formula $1/94$(g/mol)=10.6 mmol/g. Using poly metal having n charge as R, 20 —COOR is given expression of —COO $(M)_{1/n}$, —COOR content can be computed as same. If the absorbent cross-linked polymer comprising compounds such as starch, PVA, surfactant and so on, or monomer not containing —COOR, content of the absorbent cross-linked polymer can be suitably corrected. —COOR content of an absorbent cross-linked polymer can be found by any of the known methods of analysis such as neutralization titration with sodium polyacrylate having a known —COOR group content as the standard or NMR elemental analysis, X-ray fluorimetry. Incidentally, since the absorbent resin generally has a water content of not more than 10% by weight, the computation of the —COOR group content of the absorbent resin must be suitably corrected with respect to this water content. It is essential that the absorbent resin of this invention should contain —COOR groups at a higher concentration than the partially neutralized sodium polyacrylate (about 11 mmol/g) or the partially neutralized potassium polyacrylate (about 10 mmol/g) copiously used in the commercially available absorbent resins.

(II) Method of production of an absorbent polymer

It is obtained by the following (1)–(4) methods, preferably by the (1)–(3) methods.

(1) A method for obtaining the absorbent cross-linked polymer by preparing an aqueous —COOR group-containing monomer solution containing a copolymerizing cross-linking agent and adapted to acquire a —COOR group content of 12 mmol/g or more and furnish a molecular ratio of —COOH/—COOR of not more than 0.5 subsequent to polymerization, polymerizing the aqueous solution, drying the resultant polymer in the form of a gel absorbing water, and optionally pulverizing the dried polymer.

(2) A method for obtaining the absorbent cross-linked polymer by polymerizing an aqueous —COOR acid group-containing monomer solution and, during the subsequent neutralization of not less than 50 mol % of the base of the resultant polymer, neutralizing the resultant polymer with a salt until the —COOR group content of the polymer reaches a level of 12 mmol/g or more, drying the resultant polymer in the form of a gel absorbing water, and optionally pulverizing the dried polymer.

(3) A method for obtaining the absorbent cross-linked polymer by preparing an aqueous —COOR group-containing monomer solution adapted to acquire a —COOR group content of 12 mmol/g or more and furnish a molecular ratio of —COOH/—COOR of not more than 0.5 subsequent to polymerization, polymerizing the aqueous solution, subsequently causing a compound having a plurality of functional groups capable of reacting with a —COOR group to react with the polymer thereby introducing a cross-linked structure into the polymer thereby, and optionally drying this polymer.

(4) A method which comprises preparing the ester compound of the aforementioned —COOR group-containing monomer adapted to acquire a —COOR group content of 12 mmol/g or more and furnish a molecular ratio of —COOH/—COOR of not more than 0.5 subsequent to saponification of the polymer, polymerizing the ester compound, and saponifying the polymer before or after being cross-linked.

Salt used for neutralizing of monomer are, for example, solution of lithiumhydroxide, sodiumhydroxide, calciumhydroxide, inorganic amine such as hydroxyl amine, organic amine such as monoethanol amine, dimethanolamine, triethanolamine.

So long as the produced absorbent cross-linked polymer contains —COOR groups in a concentration of 12 mmol/g or more and furnishes a molecular ratio of —COOH/—COOR of not more than 0.5., the step of neutralizing the base and the introduction of the cross-linked structure may be carried out at an arbitrary stage before, after, or during the polymerization.

As more specific preferred embodiments of this invention for the synthesis of the absorbent cross-linked polymer of this invention, the following (a) - (e) methods, preferably the (a) or (d) methods, may be cited. Preferably, in this invention, the (a)–(d) methods are used for increasing the surface area of the absorbent resin and the (b) method specializing form polymerization is used for obtaining an absorbent resin having a large surface area and containing fine powder sparingly.

(a) A method which polymerizes an aqueous lithium acrylate solution containing a copolymerizing cross-linking monomer and having a degree of neutralization in the range of 50–100 mol % in the presence of a polymerization initiator in a state having bubbles of inert gas dispersed.

(b) A method which polymerizes an aqueous lithium acrylate solution containing a copolymerizing cross-linking monomer and having a degree of neutralization in the range of 50–100 mol % in the presence of a polymerization initiator and a surfactant in a state having bubbles of inert gas dispersed.

(c) A method which subjects an aqueous lithium acrylate solution containing a copolymerizing cross-linking monomer and having a degree of neutralization in the range of 50–100 mol % to reversed-phase suspension polymerization in an organic solvent in the presence of a polymerization initiator and a surfactant.

(d) A method which polymerizes an aqueous acrylic acid solution containing a copolymerizing cross-linking monomer in the presence of a polymerization initiator and, subsequent to the polymerization, adds an aqueous solution of lithium carbonate or lithium hydroxide to the resultant polymerization product to neutralize 50–100 mol % of the acid base.

(e) A method which obtains a lithium salt of polyacrylic acid by polymerizing an acrylic ester and further saponifying it before or after the resultant polymer being cross-linked, and optionally ion-exchanging the product of saponification.

(II-a) —COOR containing monomer

The —COOR containing monomers which are simultaneously used for producing the absorbent cross-linked polymer mentioned above may be two or more monomers selected from among maleic acid, fumaric acid, itaconic acid, mesaconic acid, citraconic acid, and acrylic acid. Salt of carboxyl group containing monomer contains the monomer of salt mentioned above. So long as these monomers allow production of an absorbent cross-linked polymer containing —COOR groups in a concentration of 12 mmol/g or more and having a molecular ratio of —COOH/—COOR of not more than 0.5, they may be suitably used in combination with other monomers capable of copolymerizing therewith. As concrete examples of such other monomers, sulfonic acid group-containing monomers such as 2-(meth) acryloyl ethane sulfonic acid, 2-(meth)acryloyl propane sulfonic acid, 2-(meth)-acrylamide-2-methyl propane sulfonic acid, vinyl sulfonic acid, and styrene sulfonic acid, salts thereof with such alkali metals as lithium, sodium, and potassium, and ammonium salts thereof; nonionic hydrophilic group-containing monomers such as (meth)-acrylamide, N-substituted (meth)acrylamide, 2-hydroxyethyl (meth)acrylate, 2-hydroxypropyl (meth) acrylate, methoxypoly-ethylene glycol (meth)acrylate, polyethylene glycol (meth)-acrylate, N-vinyl pyrrolidone, and N-vinyl acetamide; amino group-containing unsaturated monomers such as N,N-dimethylamino-ethyl (meth) acrylate, N,N-dimethylaminopropyl (meth)acrylate, and N,N-dimethylaminopropyl (meth) acrylamide and the products of quaternization thereof; and acrylic esters such as methyl (meth)-acrylate, ethyl (meth)acrylate, and butyl (meth)acrylate and hydrophobic monomers such as vinyl propionate may be cited.

(II-b) Copolymerizing cross-linked monomer

The copolymerizing cross-linking monomers which are usable preferably for the synthesis of an absorbent cross-linked polymer in this invention include ethylene glycol di(meth)acrylate, diethylene glycol di(meth)acrylate, triethylene glycol di(meth)-acrylate, propylene glycol di(meth) acrylate, polyethylene glycol di(meth)acrylate, trimethylol propane di(meth)acrylate, trimethylol propane tri(meth) acrylate, pentaerythritol di(meth)acrylate, pentaerythritol tri (meth)acrylate, pentaerythritol tetra(meth)-acrylate, N,N'-methylene bis(meth)acrylamide, triallyl isocyanurate, trimethylol propane di (meth) allyl ether, triallyl amine, tetraallyloxy ethane, and glycerol propoxy triacrylate, for example. The amount of such copolymerizing cross-linking monomer to be advantageously used is in the range of 0 to 2 parts by weight, preferably 0.001–1 part by weight, based on 100 parts by weight of the —COOR group-containing monomer. If the amount of the cross-linking monomer is not more than 0.001 part by weight, the proportion of the water-soluble component in the produced absorbent cross-linked polymer will possibly increase to the extent of preventing the polymer from securing fully sufficient capacity for absorption and speed of absorption under pressure. Conversely, if the amount of the cross-linking monomer exceeds 2 parts by weight, the cross-link density in the produced polymer will possibly increase too much for the produced absorbent cross-linked polymer to acquire a fully satisfactory ratio of water absorption capacity.

(II-c) Polymerization initiator

The polymerization initiators which are preferably usable in the synthesis of an absorbent cross-linked polymer of this invention include azo compounds such as 2,2'-azobis(2-amidinopropane) dihydrochloride; peroxides such as ammonium persulfate, potassium persulfate, sodium persulfate, hydrogen peroxide, benzoyl peroxide, cumene hydroperoxide, and di-t-butyl peroxide; and redox initiators produced by combining the peroxides mentioned above with such reducing agents as sulfites, hydrogen sulfites, thiosulfates, formamidine sulfinic acid, and ascorbic acid, for example. These polymerization initiators may be used either singly or in the form of a mixture of two or more members.

The amount of the polymerization initiator to be used for the —COOR group-containing monomer falls in the range of 0.001–5 parts by weight, preferably 0.01–1 part by weight, based on 100 parts by weight of the —COOR group-containing monomer, though it is variable with the combination of the monomer with the polymerization initiator. If the amount of the polymerization initiator to be used is not more than 0.001 part by weight, the amount of the unaltered monomer will increase and consequently, the amount of the residual monomer in the produced absorbent cross-linked polymer will proportionately increase. Conversely, if the amount of the polymerization initiator exceeds 5 parts by weight, the polymerization will not be easily controlled and the amount of the water-soluble component in the produced absorbent cross-linked polymer will increase unduly.

The temperature at which the polymerization is initiated falls in the range of 0–70° C., preferably 10–65° C., though it is variable with the kind of polymerization initiator to be used. The polymerization temperature in the process of reaction is in the range of 20–110° C., preferably 30–90° C. If the temperature at the start of polymerization or the polymerization temperature in the process of reaction deviate from the ranges mentioned above, such disadvantages as (a) an increase in the amount of the residual monomer in the produced absorbent cross-linked polymer and (b) a decrease in the ratio of water absorption capacity of the absorbent cross-linked polymer due to an advance of excessive self-cross-linking reaction will possibly ensue.

(II-d) Surfactant

The surfactants which are optionally used for synthesizing a preferred absorbent cross-linked polymer of this invention by the (B) and (C) method mentioned above include anionic surfactants, nonionic surfactants, cationic surfactants and amphoteric surfactants, for example.

Specifically, the anionic surfactants which are usable include fatty acid salts such as mixed fatty acid sodium soap, half cured beef tallow fatty acid sodium soap, sodium stearate soap, potassium oleate soap, and castor oil potassium soap; alkyl sulfuric ester salts such as sodium lauryl sulfate, higher alcohol sodium sulfate, sodium lauryl sulfate, and triethanol amine lauryl sulfate; alkylbenzene sulfonates such as sodium dodecylbenzene sulfonate; alkyl naphthalene sulfonates such as sodium alkylnaphthalene sulfonate; alkyl sulfosuccinates such as sodium dialkyl sulfosuccinate; alkyl diphenyl ether disulfonates such as sodium alkyl diphenyl ether disulfonate; alkyl phosphates such as potassium alkyl phosphate; polyoxyethylene alkyl (or alkylallyl) sulfuric ester salts such as sodium polyoxyethylene lauryl ether sulfate, sodium polyoxyethylene alkyl ether sulfate, polyoxyethylene alkyl ether sulfuric acid triethanol amine, and sodium polyoxyethylene alkyl phenyl ether sulfurate; special reaction type anion surfactants; special carboxylic acid type surfactants; naphthalene sulfonic acid formalin condensates such as sodium salts of β-naphthalenesulfonic acid formalin condensate and sodium salts of special aromatic sulfonic acid formalin condensate; special polycarboxylic acid type high molecular surfactants; and polyoxyethylene alkyl phosphoric esters, for example.

Then, the nonionic surfactants which are usable herein include polyoxyethylene alkyl ethers such as polyoxyethylene lauryl ether, polyoxyethylene cetyl ether, polyoxyethylene stearyl ether, polyoxyethylene oleyl ether, and polyoxyethylene higher alcohol ether; polyoxyethylene alkyl aryl ethers such as polyoxyethylene nonylphenyl ether; polyoxyethylene derivatives; sorbitan fatty acid esters such as sorbitan monolaurate, sorbitan monopalmitate, sorbitan monostearate, sorbitan tristearate, sorbitan monooleate, sorbitan trioleate, sorbitan sesquioleate, and sorbitan distearate;

polyoxyethylene sorbitan fatty acid esters such as polyoxyethylene sorbitan monolaurate, polyoxy-ethylene sorbitan monolaurate, polyoxyethylene sorbitan monopalmitate, polyoxyethylene sorbitan monostearate, polyoxy-ethylene sorbitan tristearate, polyoxyethylene sorbitan monooleate, and polyoxyethylene sorbitan trioleate; polyoxy-ethylene sorbitol fatty acid esters such as tetraoleic acid polyoxyethylene sorbit; glycerin fatty acid esters such as glycerol monostearate, glycerol monooleate, glycerol fatty acid ester such as self-emulsifying type glycerol monostearate; polyoxyethylene fatty acid esters such as polyethylene glycol monolaurate, polyethylene glycol monostearate, polyethylene glycol distearate, and polyethylene glycol monooleate; polyoxyethylene alkyl amines; polyoxyethylene cured castor oil; and alkyl alkanol amides, for example.

The cationic surfactants and amphoteric surfactants which are usable herein include alkyl amine salts such as coconut amine acetate and stearyl amine acetate; quaternary ammonium salts such as lauryl trimethyl ammonium chloride, stearyl trimethyl ammonium chloride, cetyl trimethyl ammonium chloride, distearyl dimethyl ammonium chloride, and alkylbenzyl dimethyl ammonium chloride; alkyl betaines such as lauryl betaine, stearyl betaine, and lauryl carboxymethyl hydroxyethyl imidazolinium betaine; and amine oxides such as lauryl dimethylamine oxide, for example. Use of a cationic surfactant permits importation of an antimicrobial property to the produced absorbent resin.

The other surfactants include fluorine type surfactants. Use of a fluorine type surfactant allows an aqueous monomer solution to retain bubbles of inert gas stably dispersed therein for a long time. An ordinary surfactant which has the oleophilic group thereof converted to a perfluoroalkyl group by substitution of the hydrogen atom thereof by a fluorine atom, for example, acquires a notably fortified surface activity.

(II-e) Method of polymerization

In the present invention, the method of polymerization which is employed preferably for notably heightening the speed of absorption is the (A) or (B) method of polymerization mentioned above, i.e. a method which comprises causing an aqueous monomer solution to have bubbles dispersed therein optionally by the use of such a surfactant as mentioned above and subjecting the monomer to foam polymerization. The volume of the aqueous monomer solution which has the bubbles dispersed therein at this time is not less than 1.02 times, preferably not less than 1.08 times, and more preferably not less than 1.11 times, the volume of the aqueous solution which has not yet induced dispersion of bubbles. When the volume falls in this range, the produced absorbent resin is enabled to acquire a prominent increase in the speed of absorption.

(II-f) Absorbent cross-linked polymer

In the present invention as concrete examples of the absorbent cross-linked polymer containing —COOR groups in a concentration of 12 mmol/g or more and having a molecular ratio of —COOH—COOR of not more than 0.5 as contemplated by this invention, polymaleates salts such as cross-linked lithium polymaleate, cross-linked ammonium polymaleate, or cross-linked sodium polymaleate having a degree of neutralization in the range of 50–100 mol % respectively, cross-linked potassium polymaleate having a degree of neutralization in the range of 50–66.4 mol %, cross-linked lithium polyfumarate, cross-linked ammonium polyfumarate, or cross-linked sodium polyfumarate having a degree of neutralization in the range of 50–100 mol %, cross-linked potassium polyfumarate having a degree of neutralization in the range of 50–66.4 mol % respectively; and cross-linked lithium polyitaconate or cross-linked ammonium polyitaconate having a degree of neutralization in the range of 50–100 mol %, cross-linked sodium polyitaconate having a degree of neutralization in the range of 50–83.2 mol %, cross-linked lithium polymesaconate or cross-linked ammonium polymesaconate having a degree of neutralization in the range of 50–100 mol %, cross-linked sodium polymesaconate having a degree of neutralization in the range of 50–83.2 mol %, cross-linked lithium polycitraconate or cross-linked ammonium polycitraconate having a degree of neutralization in the range of 50–100 mol %, cross-linked sodium polycitraconate having a degree of neutralization in the range of 50–83.2 mol %, and cross-linked lithium polyacrylate having a degree of neutralization in the range of 50–100 mol % may be cited.

In the absorbent cross-linked polymers mentioned above, those of ammonium salts have the possibility of liberating ammonia in consequence of decomposition when they are heated. A preferred absorbent cross-linked polymer, therefore, is at least one member selected from among cross-linked lithium polymaleate or cross-linked sodium polymaleate having a degree of neutralization in the range of 50–100 mol %, cross-linked potassium polymaleate having a degree of neutralization in the range of 50–66.4 mol %, cross-linked lithium polyfumarate or cross-linked sodium polyfumarate having a degree of neutralization in the range of 50–100 mol %, cross-linked potassium polyfumarate having a degree of neutralization in the range of 50–66.4 mol %, cross-linked lithium polyitaconate having a degree of neutralization in the range of 50–100 mol %, cross-linked sodium polyitaconate having a degree of neutralization in the range of 50–83.2 mol %, cross-linked lithium polyisaconate having a degree of neutralization in the range of 50–100 mol %, cross-linked sodium polymesaconate having a degree of neutralization in the range of 50–83.2 mol %, cross-linked lithium polycitraconate having a degree of neutralization in the range of 50–100 mol %, cross-linked sodium polycitraconate having a degree of neutralization in the range of 50–83.2 mol %, and cross-linked lithium polyacrylate having a degree of neutralization in the range of 50–100 mol %.

A more preferred absorbent cross-linked polymer is at least one member selected from among cross-linked lithium polymaleate or cross-linked sodium polymaleate having a degree of neutralization in the range of 50–100 mol %, cross-linked lithium polyfumarate or cross-linked sodium polyfumarate having a degree of neutralization in the range of 50–100 mol %, cross-linked lithium polyitaconate having a degree of neutralization in the range of 50–100 mol %, cross-linked sodium polyitaconate having a degree of neutralization in the range of 50–83.2 mol %, cross-linked lithium polymesaconate having a degree of neutralization in the range of 50–100 mol %, cross-linked sodium polymesaconate having a degree of neutralization in the range of 50–83.2 mol %, cross-linked lithium polycitraconate having a degree of neutralization in the range of 50–100 mol %, cross-linked sodium polycitraconate having a degree of neutralization in the range of 50–83.2 mol %, and cross-linked lithium polyacrylate having a degree of neutralization in the range of 50–100 mol %. The most preferred of all the absorbent cross-linked polymers is cross-linked lithium polyacrylate having a degree of neutralization in the range of 50–100 mol %.

The absorbent cross-linked polymer which can be used in this invention is allowed, on fulfilling the requirement that it be an absorbent cross-linked polymer containing —COOR groups in a concentration of 12 mmol/g or more and having a molecular ratio of —COOH/—COOR of not more than 0.5, to be used 2 or more alkali metal salts and/or ammonium salts which contain , for example, lithium salt, sodium salt and so on for neutralizing carboxyl groups.

(II-g) Method for drying

The hydrated gel polymer which is obtained during or after the reaction of polymerization can be transformed into an absorbent cross-linked polymer highly suitable for this invention by a pertinent method which comprises crushing the gel absorbing water into fragments having a particle diameter in the approximate range of 0.1 mm—about 50 mm and then drying the fragments. Though the temperature at which the fragments are dried is not particularly limited, it generally falls in the range of 100–250° C., preferably in the range of 120–200° C., for example. The duration of drying is not particularly limited but suitably decided generally in the approximate range of 10 seconds—five hours, more advantageously in the approximate range of one minute—two hours.

The means for drying the fragments is not particularly limited. Various methods such as drying by heating, drying with hot air, drying under a vacuum, drying with infrared ray, drying with microwave, drying with a drum drier, dehydration by azeotropic distillation with a hydrophobic organic solvent, and high-humidity drying by the use of hot steam can be employed. A preferred absorbent cross-linked polymer for this invention has a porous texture. The holes in the polymer have an average pore diameter in the range of 10–500 $\mu$m, preferably in the range of 20–400 $\mu$m. The average pore diameter of a given absorbent cross-linked polymer can be determined by subjecting the cross-section of a dry sample to image analysis by the use of an electron $\mu$mcope. The porous polymer can be produced by the aforementioned (A) or (B) method of foam polymerization.

(i) Form of absorbent cross-linked polymer and BET specific area

The absorbent cross-linked polymer to be effectively used in this invention may be in any arbitrary form which is selected from among the forms of fibers, spheres, granules, scales, porous particles, and crushed fragments. With consideration for the absorption properties, the polymer is preferred to be in the form of spheres or porous particles having an average particle diameter in the range of 10–1000 $\mu$m. More preferably, it is in the form of particles having an average particle diameter in the range of 100–600 $\mu$m. The specific surface area of these particles is generally 0.035 m$^2$/g or more, preferably 0.040 m$^2$/g or more, and more preferably 0.05 m$^2$/g or more, more preferably 0.08 m$^2$/g or more, especially 0.10 m$^2$/g or more. In this invention, the increase of the surface area may be attained by either decreasing the particle diameter or employing foam polymerization for the production of the polymer. Preferably the foam polymerization is adopted for the purpose of decreasing the content of fine powder having particle diameters of 150 $\mu$m or less. The content of fine powder is preferably 20 wt % or less, more preferably 10 wt % or less, and more more preferably not more than 5 wt %. In the context of the present invention, the BET specific area is intended to be mesured by measurement thereof described in Example.

(III) Absorbent resin

It has been found to be particularly suitable for a disposable diaper which enjoys an improved ratio of water absorption capacity under pressure to artificial urine under a load of 100 g/cm$^2$, suffers an only sparing decline of the ratio of water absorption capacity under pressure owing to a load, and manifests a high pressure-resistant absorption ratio. From the standpoint of securing a pressure-resistant absorbent resin of this invention, it is essential to use a covalent bond-forming cross-linking agent as a compound having plural of functional groups capable of reacting with —COOR groups and it is preferable to lower the ratio of water absorption capacity under no load of the absorbent cross-linked polymer by the agency of the covalent bond-forming cross-linking agent to 0.9–0.3 times the level which existed prior to the surface cross-linking.

If the decrease of the ratio of water absorption capacity under no load is not more than 0.9 times the level which existed before the surface cross-linking, the improvement of the ratio of water absorption capacity under pressure to artificial urine under a load of 100 g/cm$^2$ will not be sufficient even when an absorbent cross-linked polymer containing —COOR groups in a concentration of 12 mmol/g or more and having a molecular ratio of —COOH/—COOR of not more than 0.5 is used and the pressure-resistant absorption ratio will be possibly insufficient. If the decrease of the ratio of water absorption capacity under no load declines to below 0.3 times the level which existed before the cross-linking, the produced polymer will be deficient in the ratio of water absorption capacity and will possibly suffer from an inferior speed of absorption. For the sake of securing the pressure-resistant absorbent resin contemplated by the present invention, it suffices to adjust suitably the kind and amount of a cross-linking agent and the temperature and duration of heating so that the ratio of water absorption capacity under no load may fall in the range of 0.9–0.3 times, preferably in the range of 0.85–0.5 times, and more preferably in the range of 0.8–0.6 times, the level which existed before the surface cross-linking. In the context of the present invention, the ratio of water absorption capacity of absorbent cross-linked polymer and absorption resin under pressure is intended to be measured by measurement thereof described in Example.

(III-a) Compound having a plurality of functional groups capable of reacting with a —COOR group The absorbent resin in this invention is preferred to be subjected to a surface cross-linking treatment with a compound having a plurality of functional groups capable of reacting with —COOR groups in the proximity of the surface of the resin. The degree in which the surface cross-linking treatment is effected in the proximity of the surface can be confirmed by visually examining the cross section of a sample resin by a competent known method such as, for example, IR. The method for carrying out this surface cross-linking treatment is not particularly limited. The absorbent resin is preferably obtained by a method which comprises adding as a surface cross-linking agent 0.001–10 parts by weight of a compound having a plurality of functional groups capable of reacting with COOR groups to 100 parts by weight of an absorbent cross-linked polymer containing —COOR groups in a concentration of 12 mmol/g or more and having a molecular ratio of —COOH/—COOR of not more than 0.5. and heating the resultant mixture.

The compounds having a plurality of functional groups capable of reacting with —COOR groups and advantageously usable for this invention include polyhydric alcohol compounds such as ethylene glycol, diethylene glycol, propylene glycol, triethylene glycol, tetraethylene glycol, polyethylene glycol, 1,3-propane diol, dipropylene glycol, 2,3,4-trimethyl-1,3-pentane diol, polypropylene glycol, glycerin, polyglycerin, 2-butene-1, 4-diol, 1,4-butane diol, 1,5-pentane diol, 1,6-hexane diol, 1,2-cyclohexane dimethanol, 1,2-cyclohexane diol, trimethylol propane, diethanol amine, triethanol amine, polyoxypropylene, oxyethylene-oxypropylene block copolymer, pentaerythritol, and sorbitol; epoxy compounds such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, and glycidol; polyamine compounds such as ethylene diamine, diethylene triamine, triethylene tetramine, tetraethylene pentamine, pentaethylene hexamine, polyethylene imine, and polyamide polyamine; haloepoxy compounds such as epichlorohydrin, epibromohydrin, and a-methyl epichlorohydrin; condensates of the polyamine compounds mentioned above with the haloepoxy compounds mentioned above; polyisocyanate compounds such as 2,4-tolylene diisocyanate and hexamethylene diisocyanate; polyoxazoline compounds such as 1,2-ethylenebisoxazoline; silane coupling agents such as γ-glycidoxy propyl trimethoxy silane and γ-aminopropyl trimethoxy silane; and alkylene carbonate compounds such as 1,3-dioxolan-2-on, 4-methyl-1,3-dioxolan-2-on, 4,5-dimethyl-1,3-dioxolan-2-on, 4,4-dimethyl-1,3-dioxolan-2-on, 4-ethyl-1,3-dioloxolan-2-on, 4-hydroxymethyl-1,3-dioxolan-2-on, 1,3-dioxan-2-on, 4-methyl-1,3-dioxan-2-on, 4,6-dimethyl-1,3-dioxan-2-on, and 1,3-dioxolan-2-on, polymethanol suh as aluminum chloride, potassium chloride aluminum sulfate, for example. These are not particularly exclusive examples. Among other examples of the compound containing a plurality of functional groups capable of reacting —COOR groups which are cited above, polyhydric alcohol compounds, epoxy compounds, polyamine compounds, condensate of polyamine compounds with haloepoxy compounds, and alkylene carbonate compounds prove to be particularly desirable.

In the compounds cited above, this invention prefers to use a covalent bond-forming cross-linking agent capable of forming a covalent bond with —COOR groups in the absorbent resin from the standpoint of obtaining a pressure-resistant absorbent resin of this invention which has been found to manifest an increased ratio of water absorption capacity under high pressure to artificial urine under a load of 100 g/cm$^2$, only a sparing decline in the ratio of water absorption capacity under pressure owing to a load, and a high pressure-resistance ratio, and prove to be suitably used for disposable diapers and also from the standpoint of ensuring production of an absorbent resin having a large surface area 0.03 g/m$^2$ or more and manifesting a high ratio of water absorption capacity under high pressure. Among other covalent bond-forming cross-linking agents which are available at all, at least one member selected from among polyhydric alcohol compounds, epoxy compounds, polyamine compounds, and alkylene carbonate compounds is advantageously used. These compounds having a plurality of functional groups capable of reacting with —COOR groups may be used either singly or in the form of a mixture of two or more members.

When two or more compounds having a plurality of functional groups capable of reacting with —COOR groups are used in combination, the absorbent resin excelling in absorption properties to a greater extent can be obtained by adopting for the combination such compounds as severally possess a plurality of functional groups capable of reacting with —COOR groups such as, for example, a first surface cross-linking agent and a second surface cross-linking agent having mutually different solubility parameters (SP values) as disclosed in U.S. Pat. No. 5,422,405. The term "solubility parameter" refers to a numerical value which is generally used as a factor representing characteristics of a compound. For the solubility parameter mentioned above, this invention contemplates adopting the numerical value of the solubility parameter, δ (cal/cm$^3$)$^{1/2}$, of a relevant solvent shown in Polymer Handbook, 3rded., (published by Wiley Interscience Co.), pp. 527–539. For the solubility parameter of a solvent which is not shown in the pages mentioned above, this invention contemplates adopting the numerical value which is derived from substituting the Hoy's cohesive energy constant shown in page 525 ibidem for the relevant variable in the Small's formula shown in page 524 ibidem.

The first surface cross-linking agent is preferred to be a compound which is capable of reacting with the functional groups possessed by the polymer and which possesses a solubility parameter of not less than 12.5 (cal/cm$^3$)$^{1/2}$, preferably not less than 13.0 (cal/cm$^3$)$^{1/2}$. Specifically, the compounds answering this description include ethylene glycol, propylene glycol, glycerin, pentaerythritol, sorbitol, ethylene carbonate (1,3-dioxolan-2-on), and propylene carbonate (4-methyl-1,3-dioxolan-2-on), for example. These compounds are not exclusive examples. For the first surface cross-linking agent, one member or a mixture of two or members suitably selected from the group mentioned above can be used.

Then, the second surface cross-linking agent is preferred to be a compound which is capable of reacting with the functional groups possessed by the polymer and which possesses a solubility parameter of not more than 12.5 (cal/cm$^2$)$^{1/2}$, preferably falling in the range of 9.5 (cal/cm$^3$)$^{1/2}$–12.0 (cal/cm$^3$)$^{1/2}$. Specifically, the compounds which answer the description include diethylene glycol, triethylene glycol, tetraethylene glycol, 1,3-butane diol, 1,4-butane diol, 1,5-pentane diol, 1,6-hexane diol, 2,5-hexane diol, trimethylol propane, ethylene glycol diglycidyl ether, polyethylene glycol diglycidyl ether, glycerol polyglycidyl ether, polyglycerol polyglycidyl ether, propylene glycol diglycidyl ether, and polypropylene glycol diglycidyl ether, for example. These compounds are not exclusive examples. For the second surface cross-linking agent, one member or a mixture of two or members suitably selected from the group mentioned above can be used. The amount to be used of the compound having a plurality of functional groups capable of reacting —COOR groups may be suitably set in the range of 0.001–10 parts by weight, preferably in the range of 0.01–5 parts by weight, based on 100 parts by weight of the absorbent cross-linked polymer. The amount of the surface cross-linking agents mentioned to be used, namely the total amount of the first surface cross-linking agent and the second surface cross-linking agent is preferred to be in the range of 0.001–10 parts by weight, preferably in the range of 0.01–5 parts by weight, based on 100 parts by weight of the solids content of the ultimately obtained absorbent resin, though variable with the kinds of cross-linking agent and the combination thereof.

When the amount to be used of the surface cross-linking agents mentioned above is within the range mentioned above, the cross-link density in the proximity of the surface of the produced absorbent resin is allowed to be higher than in the inner part of the resin. As a result, the produced absorbent resin is enabled to excel in absorption properties under pressure irrespectively of the magnitude of a load. If the amount to be used of the cross-linking agents mentioned above is not more than 0.001 part by weight, the agents will possibly fail to bring about a fully sufficient effect of improving absorption properties under pressure. If this amount exceeds 10 parts by weight, the added cross-linking agents will not be efficiently used and will prove uneconomical. The amount will tend to exceed the amount necessary for the formation of the optimum cross-linked structure for an absorbent and also tend to degrade the ratio of water absorption capacity to an excess.

If the amount to be used of the compound having a plurality of functional groups capable of reacting with —COOR groups is not more than 0.001 part by weight, the compound will be hardly capable of heightening the cross-link density in the proximity of the surface of the produced absorbent resin. If this amount exceeds 10 parts by weight, the compound will form an excess supply, do no good to economy, and possibly render difficult the control of the cross-link density at a proper value. And —COOR contents can be decreased greatly. By using the compound having a plurality of functional groups capable of reacting with —COOR groups in the preferred range mentioned above, the absorption properties of the produced polymer with respect to such bodily humors as urine, perspiration, and menstrual fluid (aqueous liquids) can be further improved.

(III-b) Method for adding a surface cross-linked agent As means for adding a compound having a plurality of functional groups capable of reacting with —COOR groups to an absorbent cross-linked polymer of this invention containing —COOR groups in a concentration of 12 mmol/g or more and having a molecular ratio of —COOH/—COOR of not more than 0.5. and manifesting an improved charge density, the following (1)–(4) methods are used, for example.

(1) A method which consists in mixing an absorbent cross-linked polymer with a compound having a plurality of functional groups capable of reacting with —COOR groups without using any solvent.

(2) A method which comprises causing an absorbent cross-liked polymer to be dispersed in a hydrophobic solvent such as cyclohexane or pentane and then mixing the resultant dispersion with a solution of a compound having plural of functional groups capable of reacting with —COOR groups in an aqueous solvent or hydrophobic solvent.

(3) A method which comprises dissolving or dispersing a compound having plural of functional groups capable of reacting —COOR groups in a hydrophilic solvent and then spraying or dropping the resultant solution or dispersion onto an absorbent cross-linked polymer thereby inducing mixture thereof.

(4) A method which consists in adding a compound having plural of functional groups capable of reacting with —COOR groups to an absorbent cross-linked polymer having the water content thereof adjusted in a specific range.

The present invention prefers the (3) method, i.e. a method which comprises dissolving or dispersing a compound having plural of functional groups capable of reacting —COOR groups in a hydrophilic solvent and then spraying or dropping the resultant solution or dispersion onto an absorbent cross-linked polymer thereby inducing mixture thereof, over the other methods described above. Incidentally, the hydrophilic solvent mentioned above is preferred to be water or a mixture of water with an organic solvent soluble in water.

The organic solvents which answer the description given above include lower alcohols such as methyl alcohol, ethyl alcohol, n-propyl alcohol, iso-propyl alcohol, n-butyl alcohol, iso-butyl alcohol, and t-butyl alcohol; ketones such as acetone; ethers such as dioxane, adducts of ethylene oxide (EO) to monohydric alcohols; amides such as N,N-dimethyl formamide and $\epsilon$-caprolactam; and sulfoxides such as dimethyl sulfoxide, for example. These organic solvents may be used either singly or in the form of a mixture of two or more members.

The amount of the hydrophilic solvent to be used for the absorbent cross-linked polymer and the compound having a plurality of functional groups capable of reacting —COOR groups is not more than 200 parts by weight, preferably in the range of 0.01–50 parts by weight, more preferably in the range of 0.1–50 parts by weight, and particularly preferably in the range of 0.5–30 parts by weight, based on 100 parts by weight of the absorbent cross-linked polymer, though this amount depends on the combination of the absorbent cross-linked polymer and the compound having a plurality of functional groups capable of reacting with —COOR group with the hydrophilic solvent.

The mixing device to be used in mixing the absorbent cross-linked polymer with the solution of the compound having a plurality of functional groups capable of reacting with COOR groups is preferred to be endowed with a large mixing power to ensure uniform and infallible mixture thereof. The mixing devices which answer this description and promise favorable use include a cylindrical mixer, double-wall conical mixer, high-speed stirring type mixer, V-shaped mixer, ribbon type mixer, screw type mixer, fluidized-bed rotary disk type mixer, air current type mixer, twin-arm type kneader, inner mixer, pulverizing type kneader, rotary type mixer, and screw type extruder, for example.

(III-c) Method for heating

For the purpose of increasing the cross-link density in the proximity of the surface of the absorbent cross-linked polymer, the absorbent cross-linked polymer of this invention which contains —COOR groups in a concentration of 12 mmol/g or more and has a molecular ratio of —COOH/—COOR of not more than 0.5. is heated after having added a compound having a plurality of functional groups capable of reacting with —COOR groups. Though the temperature of this heating may be properly selected to suit the cross-link density to be expected, it is in the range of 40–250° C., preferably in the range of 80–220° C. This invention has established that when the reaction time is suitably selected in the range of 1–120 minutes, preferable of 3–60 minutes.

The use of an absorbent cross-linked polymer containing —COOR groups in a concentration of 12 mmol/g or more and having a molecular ratio of —COOH/—COOR of not more than 0.5 as a base polymer as contemplated by this invention results in markedly curtailing the reaction time or lowering the reaction temperature as compared with the conventional 70 mol % neutralization cross-linked sodium polyacrylate (amount of —COOR groups: 11.4 mmol/g).

(III-d) BET specific surface area

The absorbent resin of this invention which has a large specific surface area of 0.03 $m^2/g$ or more, preferably 0.035 $m^2/g$ or more, more preferably 0.04 $m^2/g$ or more and has a ratio of water absorption capacity of 25 g/g or more , preferably 28 g/g or more , more preferably 30 g/g or more to artificial urine under a load of 100 $g/cm^2$. The content of fine powder of a particle diameter of 150 $\mu$m or less, lowered to not more than 20 wt %, preferably 10 wt % or less, and more preferably 5 wt % or less. In the context of the present invention, the content of fine powder is intended to be measured by measurement thereof described in Example. The absorbent resin having a large specific surface area and a small content of fine powder is obtained by the foaming mentioned above.

It has been heretofore known to decrease the particle diameter of an absorbent resin for the purpose of enabling the absorbent resin to acquire an increase speed of absorption. When the content of fine powder not exceeding 150 $\mu$m in diameter is suffered to exceed 20 wt %, or further 30 wt %, the absorbent resin not merely yields a swelled gel which tends to clog the texture of a diaper induces the diaper to leak urine but also furnishes uniform surface cross-linkage only with difficulty and degrades the ratio of water absorption capacity under pressure. As a means for enlarging the surface area of an absorbent resin without reducing the particle diameter thereof, a method which uses a foamed absorbent resin has been proposed. Where the ratio of water absorption capacity under pressure deserves first consideration when a cross-linking treatment is given to the proximity of surface of a porous resin, since the treatment must form a high cross-link density in the surface, the surface of a porous polymer which allows no easy control of cross-link density is compelled to sacrifice its hydrophilicity. In spite of the use of the porous polymer, therefore, the surface cross-linking eventually results in lowering the speed of absorption.

Heretofore, the surface area and the ratio of water absorption capacity under pressure, particularly the ratio of water absorption capacity under high pressure, have been contradictory properties. This invention, owing to the increase of the content of —COOR groups density of 12 mmol/g or more in an absorbent resin or an absorbent cross-linked polymer, allows provision of a novel absorbent resin which incredibly manifests an exceptionally high ratio of water absorption capacity of not less than 22 g/g under high pressure even when the surface area is increased by decreasing the particle diameter or foaming the resin particles.

(IV) Pressure-resistant absorbent resin

This invention further provides a novel absorbent resin, namely a pressure-resistant absorbent resin which exhibits a ratio of water absorption capacity of 35 g/g or more to artificial urine under a no load, and a ratio of water absorption capacity of 30 g/g or more, preferably 33 g/g, to artificial urine under a pressure load of 50 g/cm$^2$, and a ratio of water absorption capacity of 22 g/g or more to artifical urine under a high pressure load of 100 g/cm$^2$, and a ratio of water absorption capacity after five minutes of 25 g/g of more under 50 g/m$^2$, and a speed of absorption of less than 20 sec. The absorbent resin of this invention contains a water-soluble component in a concentration of not more than 25 wt %, preferably not more than 15 wt %, and more preferably not more than 10 wt %. In the context of the present invention, the contains a water-soluble component is intended to be measured by measurement thereof described in Example.

(V) Pressure-resistant absorption ratio

The term "pressure-resistant absorption ratio" as used in this invention refers to the magnitude determined by the ratio: (the ratio of water absorption capacity under high pressure to artificial urine under a load of 100 g/cm$^2$)/(the ratio of water absorption capacity under pressure to artificial urine under a load of 50 g/cm$^2$). This is a novel parameter which has not attracted any attention to date.

the pressure-resistant absorbent resin in the present invention which exhibits a ratio of water absorption capacity of 30 g/g or more, preferably 35 g/g under pressure to artificial urine a load of 50 g/cm$^2$, and a pressure-resistant absorption ratio of 0.6 or more, preferably 0.7 or more, more preferably 0.75 or more, particularly preferably 0.8 or more. The sample of Example 2 of this invention which will be described herein below, for instance, manifests exceptionally stable absorption properties to such a change in load (pressure) as 0.82 of pressure-resistant ratio.

Since both ratios are low, their declines due to an increase of the load apparently contract and, as a result, the pressure-resistant absorption ratio possibly reaches a level exceeding 0.7 (as in the samples of Controls 1–3 of this invention to be described specifically herein below). The absorbent resin which has a ratio of water absorption capacity under pressure falling short of 30 g/g to artificial urine under a load of 50 g/cm$^2$, however, is incapable of withstanding the load of a standard baby and fails to accomplish any of the objects of this invention. It has been found that simply because a given absorbent resin manifests a duly high ratio of water absorption capacity under a load of 10 to some tens of g/cm$^2$ which is estimated from the standard body weight (about 10 kg) of a baby, it does not necessarily follow that this absorbent resin, when incorporated in an actual diaper, fulfills a satisfactory function.

The absorbent resins simply manifesting high ratios of water absorption capacity under pressure which have been proposed to date reach a large total. Simply because a given absorbent resin manifests a duly high ratio of water absorption capacity under a load of 10 to some tens of g/cm$^2$ which is estimated from the standard body weight (about 10 kg) of a baby, it does not necessarily follow that this absorbent resin, when incorporated in an actual diaper, fulfills a satisfactory function. It has been further established that a recently proposed conventional absorbent resin manifests a ratio of water absorption capacity of not less than 30 g/g under pressure (50 g/cm$^2$) and that even this absorbent resin has a ratio of water absorption capacity of 18 g/g at most under high pressure (100 g/cm$^2$), a magnitude decidedly insufficient for any absorbent resin. This invention has further established that the decline of the ratio of water absorption capacity under such a pressure as exceeds the load estimated from the body weight, namely the pressure-resistant absorption ratio which is determined by the ratio (the ratio of water absorption capacity under high pressure to artificial urine under a load of 100 g/cm$^2$) / (the ratio of water absorption capacity under pressure to artificial urine under a load of 50 g/cm$^2$) is extremely important for disposable diapers.

Further, it has been established that even the conventional absorbent resin which manifests a ratio of water absorption capacity of not less than 30 g/g under pressure (50 g/cm$^2$) suffers the ratio of water absorption capacity to be decreased largely by an increase of the load (pressure) and that specifically, this absorbent resin manifests the pressure-resistant absorption ratio, a magnitude defined as the ratio of the aforementioned ratio of water absorption capacity under pressure to the ratio of water absorption capacity under high pressure to artificial urine under a load of 100 g/cm$^2$, at a low level of not more than 0.6.

It has been found by the inventors' monitor test that the conventional absorbent resin manifesting a pressure-resistant absorption ratio of not more than 0.6 gives no perfect performance as a diaper even when the ratio of water absorption capacity under pressure is not less than 30 g/g to artificial urine under a load of 50 g/cm$^2$.

(VI) Additive

The absorbent resin and the pressure-resistant absorbent resin of this invention which are obtained as described above, when necessary, may incorporate therein antibacterial agent, deodorant, perfume, various species of inorganic powder, foaming agent, pigment, dye, hydrophilic short fibers, plasticizer, thickener, surfactant, oxidizing agent, reducing agent, water, and salts and consequently acquire various functions.

The inorganic powder is a substance which is inactive to aqueous liquids. As concrete examples of the inorganic powder, minute particles of various organic compounds and minute particles of clayish minerals may be cited. The inorganic powder is preferred to show moderate affinity for water and exhibit insolubility or sparing solubility to water. As concrete examples of the inorganic powder, metal oxides such as silicon dioxide and titanium dioxide, silicic acid and silicates such as natural zeolite and synthetic zeolite, kaoline, talc, clay, and bentonite may be cited. Among other inorganic powder mentioned above, silicon dioxide and silicic acids (silicates) prove to be particularly suitable. The silicon dioxide and silicic acids (silicates) whose average particle diameters determined by the Coulter counter method are not more than 200 $\mu$m, preferably not more than 20 $\mu$m, more preferably not more than 2 $\mu$m prove to be especially suitable.

The amount of the inorganic powder to be used for the absorbent resin or the pressure-resistant absorbent resin of this invention is in the range of 0.001–10 parts by weight, preferably in the range of 0.01–5 parts by weight, based on 100 parts by weight of the (pressure-resistant) absorbent resin, though it is variable with the combination of the (pressure-resistant) absorbent resin and the inorganic powder. The method of mixing the (pressure-resistant) absorbent resin and the inorganic powder is not particularly limited. The dry blending method, the wet mixing method, etc. may be adopted. Preferably, the dry blending method is adopted.

(VII) Usage (VII-a) Absorbent article

The absorbent resin or the pressure-resistant absorbent resin of this invention, when combined with such a fibrous substance as pulp, is transformed into absorbent articles. The absorbent articles include hygienic materials (bodily humor absorbing materials) such as disposable diapers and sanitary napkins, pads intended for wear by patients of incontinence, materials for protecting lacerations, and materials for cure of lacerations; absorbent articles for the urine of pet animals; materials for civil engineering and construction such as building material, water-retaining material for soil, water-preventing material, packing material, and gel water bags; food grade articles such as drip absorbents, freshness-retaining material, and refrigerating material; various industrial articles such as oil-water separating material, material for preventing food from condensation of water, and coagulating material; and agricultural and horticultural articles such as water-retaining materials for plants and soil, for example. These are not exclusive examples.

(VII-b) Disposable diaper

The disposable diaper which uses the absorbent resin or pressure-resistant absorbent resin of this invention is fabricated, for example, by sequentially superposing a back sheet made of material impervious to water, a core layer (absorbent materiel) containing the absorbent resin of this invention, and a top sheet (surface material) formed of material pervious to liquid in the order mentioned and meanwhile mixing the layers to each other and then attaching to the resultant superposed layers a gather (elastic part) and a so-called tape fastener. The term "disposable diaper" as used herein is meant to embrace such pants as are fitted with a disposable diaper and used for training infants on the habit of autonomic urination and defecation.

The absorbent resin of this invention can use of the disposable diaper which has high level core (the absorbent resin/(fiber material+absorbent resin)) so the absorbent resin has a high pressure absorbent ratio, core concentration is 30–100% preferably 40–95%, more preferably 50–90% to get thin type dispersible diaper.

(VIII) Effect

The absorbent resin or the pressure-resistant absorbent resin of this invention manifests the outstanding effects enumerated in the following items (1)–(5).

(1) The absorbent resin, in the process of manufacture, offers enhanced reactivity with a compound having a plurality of functional groups capable of reacting with the —COOR groups present in the proximity of surface of the polymer without reference to the shape of a base polymer and, consequently, permits a reduction of the duration of a heat treatment for the surface cross-linking treatment without being affected by the shape of the polymer.

(2) Even the base polymer of a porous texture, after the surface cross-linking treatment, suffers no decline of the affinity thereof for an aqueous liquid and, consequently, allows a marked addition to the speed of absorption.

(3) The produced absorbent resin enjoys heretofore unattainable great improvements in absorption properties as aptly evinced by ample reconciliation between the two frequently contradictory factors, i.e. the ratio of water absorption capacity under pressure and the speed of absorption.

(4) The novel pressure-resistant absorbent resin is provided which manifests such a high ratio of water absorption capacity under pressure even under a load of 100 g/cm$^2$ as has never been found in the conventional absorbent resin, suffers only a sparing decline of the capacity for absorption in spite of a great increase of load from 50 g/cm$^2$ to 100 g/cm$^2$, and manifests an outstanding capacity for absorption under a load of any magnitude.

(5) The disposable diaper is provided which uses a pressure-resistant absorbent resin manifesting a ratio of water absorption capacity of not less than 30 g/g under pressure to artificial urine under a load of 50 g/cm$^2$ and a pressure-resistant absorption ratio of not less than 0.6, the pressure-resistant absorption ratio being defined as the ratio of the aforementioned ratio of water absorption capacity under pressure to the ratio of water absorption capacity under high pressure to artificial urine under a load of 100 g/cm$^2$. The disposable diaper consequently provided, therefore, manifests a high ratio of water absorption capacity under pressure, suffers leakage of urine only sparingly, and enjoys a large capacity for absorption even when the load of a baby's body weight is constantly varied due to the incessant movement of the baby, it has provided a thin type disposable diaper thereby concentration of absorbent resin in core (absorbent).

(6) The absorbent resin having such a high ratio of water absorption capacity of 22 g/g under high pressure as has never been attained in spite of a large specific surface area of not less than 0.03 m$^2$/g has been obtained for the first time in the art. It has been found that this novel absorbent resin is unusually suitable for a disposable diaper. This absorbent resin is preferred to have the content of fine powder of particle diameter of not more than 150 $\mu$m lowered to a level of not more than 20 wt %, preferably not more than 10 wt % Incidentally, the absorbent resin having a large surface area and a small content of fine powder is obtained by the foaming described above.

EXAMPLES

Now, this invention will be described more specifically below with reference to working examples and controls. It should be noted, however, that the scope of this invention is not limited to or by the following examples. Wherever % is mentioned in the working examples and controls, it is meant as weight % unless otherwise specified. By the same token, the term "part" is means as part by weight.

The speed of absorption, ratio of water absorption capacity, ratio of water absorption capacity under pressure, and content of water-soluble component of the absorbent cross-linked polymer and (pressure-resistant) absorbent resin were determined by the following methods. The pressure-resistant absorbent resin and absorbent resin will be referred to collectively as absorbent resin hereinafter.

(1) Speed of absorption of absorbent cross-linked polymer and absorbent resin.

The artificial urine was prepared by dissolving 2.0 g of potassium chloride, 2.0 g of sodium sulfate, 0.8 g of ammonium dihydrogenphosphate, 0.15 g of diammonium hydrogenphosphate, 0.19 g of calcium chloride, 0.23 g of magnesium chloride in 1 liter of deionized water.

In a cylindrical cup of polypropylene measuring 50 mm in inside diameter and 70 mm in height, 1.00 g of a given absorbent cross-linked polymer or absorbent resin was placed. Next, 15 g of the artificial urine was poured into the cup. Then, the interval from the time the artificial urine was poured in till the time the artificial urine vanished after being wholly absorbed by the absorbent resin or absorbent cross-linked polymer was measured. This measurement was performed up to three repetitions and the average of the three measurements was reported as the speed of absorption (seconds).

(2) Ratios of water absorption capacity of absorbent cross-linked polymer and absorbent resin under no load A pouch resembling a tea bag (6 cm×6 cm) was uniformly filled with 0.200 g of the absorbent cross-linked polymer or absorbent resin and, with the opening thereof heat sealed, immersed in the artificial urine. After the elapse of 60 minutes thence, the pouch was pulled up, drained by a centrifugal separator at 250 G for three minutes, and weighed ($W_1$g). This procedure was repeated to find the weight ($W_0$g) of the pouch containing neither absorbent cross-linked polymer nor absorbent resin. Then, the ratio of water absorption capacity (g/g) was computed in accordance with the following formula a using the weights $W_1$ and $W_0$.

Formula a: Ratio of water absorption capacity under no load $$(g/g)=(W_1-W_0)/0.200$$

(3) Content of water-soluble component in absorbent cross-linked polymer and absorbent resin In 1000 ml of deionized water, 0.5 g of an absorbent cross-linked polymer or absorbent resin was dispersed and stirred for 16 hours. The resultant swelled cross-linked gel was passed through a filter paper. The resultant filtrate was tested for the water-soluble polymer content or the content of water-soluble component by colloidal titration to find the content of water-soluble component (wt %) in the absorbed cross-linked polymer or absorbent resin.

(4) Average particle diameter of absorbent cross-linked polymer

The average particle diameter of an absorbent cross-linked polymer was determined by classifying the absorbent cross-linked polymer with JIS standard sieves having the meshes (850 $\mu$m, 600 $\mu$m, 300 $\mu$m, 150 $\mu$m, and 106 $\mu$m), plotting the residual percentage points R consequently found on a logarithmic probability chart, and selecting the particle diameter corresponding to R=50%. This particle diameter was reported.

(5) Specific surface area of absorbent cross-linked polymer and absorbent resin

The specific surface area of an absorbent cross-linked polymer and absorbent resin were determined by the B. E. T. adsorption isotherm method using a fully automatic specific surface area measuring device (produced by Yuasa-Ionics K. K. and sold under the trademark of "4-Sorb U1"). First, about 5 g of an absorbent cross-linked polymer (a sample prepared by separating a portion consisting of particles having particle diameters in the range of 600–300 $\mu$m with the aid of JIS standard sieves) was placed in a microcell (Type: QS-400) having an inner volume of about 13 cm$^2$. The microcell containing the sample was heated in a stream of nitrogen gas to 150° C. until the sample was thoroughly deaerated and dehydrated. Next, the microcell containing the sample was cooled in a stream of a mixed gas consisting of helium gas and 0.1% of Krypton gas to −200° C. until the mixed gas was adsorbed to an equilibrium by the sample. Thereafter, the microcell containing the sample was warmed to room temperature to effect elimination of the sample from the mixed gas and measure the amount of the krypton-mixed gas consequently eliminated. The specific surface area of the absorbent cross-linked polymer was determined based on the amount of the krypton-mixed gas thus found. The process of adsorption—elimination of the microcell containing the sample was performed up to three repetitions. The specific surface area of the absorbent cross-linked polymer (m$^2$/g) was computed from the average of the three measurements.

(6) Bulk specific gravity of absorbent cross-linked polymer

An apparent density measuring device (adapted to meet the specification of JIS K3362 6.2, with necessary modifications) was placed horizontally on a stable bench and 100.0 g of an absorbent cross-linked polymer (sample) was placed in the upper funnel of the apparent density measuring device. The sample was left freely falling into a cup of acrylic resin having a known weight (g) and an inner volume of 100 ml (adapted to meet the specification of JIS K3362 6.2, with necessary modifications). Of the total volume of the absorbent cross-linked polymer fallen into the cup, the convex surface portion was gently removed by sliding a glass rod. Then, the weight (g) of the cup filled with the polymer was measured to the smallest unit of 0.01 g to find the weight (g) of the absorbent cross-linked polymer per 100 ml. This weight was divided by the volume of the cup and the quotient consequently found was reported as the bulk specific gravity (g/ml).

(7) Ratios of water absorption capacity of absorbent resin under pressure and under high pressure First, the measuring device used for the determination of the ratio of water absorption capacity under pressure will be briefly explained with reference to FIG. 1.

The measuring device, as illustrated in FIG. 1, is composed of a balance 1, a container 2 of a prescribed volume mounted on the balance 1, an ambient air inlet pipe 3, a conduit 4, a glass filter 6, and a measuring part 5 mounted on the glass filter 6. The container 2 is provided at the top thereof with an opening part 2*a* and on the lateral part thereof with an opening part 2*b*. The ambient air inlet pipe 3 is inserted into the opening part 2*a* and the conduit 4 is fitted to the opening part 2*b*. In the container 2, a prescribed amount of artificial urine 11 is placed. The lower end part of the ambient air inlet pipe 3 is submerged in the artificial urine 11. The glass filter 6 mentioned above measures 70 mm in diameter. The container 2 and the glass filter 6 intercommunicate via the conduit 4. The glass filter 6 is fixed so that the upper part thereof occupies a position very slightly higher than the lower end of the ambient air inlet pipe 3.

The measuring part 5 mentioned above is attached a filter paper 7, a supporting cylinder 8, a metal net 9 attached to the bottom part of the supporting cylinder 8, and a weight 10. The measuring part 5 has the filter paper 7 and the supporting cylinder 8 (namely, the metal net 9) superposed in the order mentioned on the glass filter and has the weight 10 mounted inside the supporting cylinder 8, namely, on the metal net 9. The supporting cylinder 8 has 60 mm in inside diameter. The metal net 9 is made of stainless steel and has 400 mesh (38 μm in mesh size). The metal net 9 is adapted to permit uniform dispersion of a prescribed amount of the absorbent resin. The weight 10 has the weight thereof adjusted such that a load of 50 g/cm$^2$ or 100 g/cm$^2$ may be uniformly exerted on the metal net 9, namely the absorbent resin.

The ratio of water absorption capacity under pressure was determined by using the measuring device of the foregoing construction. The method of determination will be explained below.

First, such necessary preparatory steps as placing a prescribed amount of the artificial urine 11 in the container 2 and fitting the ambient air inlet pipe 3 into the container 2 were carried out. Next, the filter paper 7 was placed on the glass filter 6. Meanwhile, parallelly to the preparatory steps, 0.9 g of the absorbent resin was uniformly spread inside the supporting cylinder 8, namely on the metal net 9 and the weight 10 was mounted on the layer of the absorbent resin. Then, on the filter paper 7, the metal net 9 or the supporting cylinder 8 having the absorbent resin and the weight 10 mounted thereon was set in place. The weight, $W_2$ (g), of the artificial urine 22 absorbed by the absorbent resin over the duration of 60 minutes following the time the supporting cylinder 8 was mounted on the filter paper 7 was found by the use of the balance 1. Then, the ratio of water absorption capacity under pressure (g/g) 60 minutes after the start of the absorption was computed according to the following formula b using the weight, $W_2$, mentioned above, to find the ratio of water absorption capacity (g/g) under pressure (50 g/cm$^2$) and the ratio of water absorption capacity (g/g) under high pressure (100 g/cm$^2$).

Formula b: Ratio of water absorption capacity under pressure (g/g)=Weight of $W_2$ (g)/weight of absorbent resin (g)

Since this determination can be carried out along the course of time, this invention elected to find the ratio of water absorption capacity (g/g) after five minutes' application of the pressure (50 g/cm$^2$) as a criterion of the speed of absorption under pressure.

(8) Pressure-resistant absorption ratio

The pressure-resistant absorption ratio was determined in accordance with the following formula c using the ratio of water absorption capacity (g/g) under pressure and the ratio of water absorption capacity (g/g) under high pressure which were found by the procedure for the determination of the ratio of water absorption capacity of an absorbent resin under pressure described in (7) above.

Formula c: Pressure-resistant absorption ratio=(Ratio of water absorption capacity under high pressure) (ratio of water absorption capacity under pressure)

(9) Content of fine powder

The content of fine powder in a given absorbent resin was determined by reducing 10 g of the absorbent resin, classifying the reduced resin with a JIS standard sieve of 150 μm, and finding the proportion (wt %) of the part of resin passing the sieve to the whole of the resin.

Referential Example 1

A partially neutralized aqueous lithium acrylate solution having uniformly dissolved therein 18.01 parts of acrylic acid, 233.94 parts of an aqueous solution containing lithium acrylate in a concentration of 25 wt %, and 0.0231 part of N,N'-methylene bis-acrylamide as a cross-linking agent (0.015 mol % based on monomer) (concentration 30 wt % and degree of neutralization 75 mol %) was prepared and deaerated with nitrogen gas. Thereafter, 1.2 parts of an aqueous 10 wt % sodium persulfate solution was added to the former aqueous solution. Then, in a nitrogen-displaced four-neck separable flask, 1 liter in inner volume, fitted with stirring vanes, thermometer, cooling tube, and dropping funnel, 700 parts of cyclohexane as a dispersion solvent and 3.333 parts of sorbitan monostearate as a surfactant (produced by Kao Corporation and sold under the trademark of "Span-60") were placed. Thereafter, by stirring the resultant mixture and meanwhile adding thereto the prepared partially neutralized aqueous lithium acrylate solution, the aqueous monomer solution was uniformly dispersed in the cyclohexane. After the aqueous monomer solution had been stably dispersed, the cyclohexane phase was heated over a water bath to 60° C. to initiate reversed-phase suspension polymerization. About 30 minutes thereafter, the polymerization reached a peak temperature (about 65° C.). Then, it was further continued for one hour. The consequently produced dispersion having spheres of a hydrated cross-linked polymer dispersed therein was deprived of the water content by azeotropic dehydration. The dry polymer thus obtained was separated from the cylohexane by filtration. The spheres of dry polymer thus obtained were washed with 200 ml of methanol at about 50° C. They were denuded of the surfactant adhering to the surface thereof by performing this procedure up to three repetitions. Finally, by drying the polymer under a reduced pressure at 70° C. for one day, an absorbent cross-linked polymer (1) of this invention containing —COOR groups in a concentration of 13.1 mmol/g and having a molecular ratio of —COOH/—COOR of 0.25 was obtained. The ratio of ratio of water absorbent capacity and content of water-soluble component were 64.8 (g/g) and 15.8 wt % respectively.

Referential Example 2

An aqueous monomer solution containing 42 parts of lithium hydroxide monohydrate, 96 parts of acrylic acid, 0.649 part of polyethylene glycol (n=8) diacrylate, 0.047 part of polyoxyethylene sorbitan monostearate (produced by Kao Corporation and sold under the trademark of "Rheodol Super TW-S120"), and 268 parts of purified water was prepared. The aqueous monomer solution was deaerated with nitrogen, cooled to 22° C., and quickly stirred so that it stably yielded as dispersed bubbles of nitrogen gas therein and increased the volume thereof to 1.08 times the volume it had assumed before the dispersion of the bubbles and meanwhile made to add 1.33 parts of an aqueous 10% sodium persulfate solution and 0.67 part of an aqueous 1% L-ascorbic acid solution. When the aqueous monomer solution was gelled about three minutes after the introduction of the polymerization initiator, the stirring was discontinued and the aqueous monomer solution was left undergoing stationary polymerization. In about 35 minutes after the introduction of the polymerization initiator, the polymerization temperature reached its peak level of 78° C. After the peak, the reaction system was heated for one hour in a hot water bath at 90° C. to terminate the polymerization. The resultant spongy gelled polymer absorbing water containing bubbles copiously was cut with scissors into cubes of about 10 mm and the porous cubes were subsequently dried in a hot air drier at 160° C. for 90 minutes. The dried cubes were pulverized with a desk-top pulverizer. The resultant powder was passed through a sieve with meshes of 850 μm.

The particles which had passed the sieve were collected to furnish an absorbent cross-linked polymer (2), 280 μm in average particle diameter, of this invention containing —COOR groups in a concentration of 12.9 mmol/g and having a molecular ratio of —COOH/—COOR of 0.25 was obtained. The ratio of water absorption capacity, speed of absorption, content of water-soluble component, bulk specific gravity, and specific surface area of the absorbent cross-linked polymer (2) were 51.0 (g/g), 14 seconds, 9.1 wt %, 0.1 (g/ml), and 0.1375 (m$^2$/g) respectively.

Referential Example 3

An aqueous monomer solution containing 42 parts of lithium hydroxide monohydrate, 96 parts of acrylic acid, 0.5192 part of polyethylene glycol (n=8) diacrylate, 0.01 part of polyoxyethylene sorbitan monostearate (produced by Kao Corporation and sold under the trademark of "Rheodol Super TW-S120"), and 282 parts of purified water was prepared. The aqueous monomer solution was deaerated with nitrogen, cooled to 12° C., and quickly stirred so that it stably yielded as dispersed bubbles of nitrogen gas therein and increased the volume thereof to 1.05 times the volume it had assumed before the dispersion of the bubbles and meanwhile made to add 1.33 parts of an aqueous 10% 2,2'-azobis(2-methylpropionamidine) dihydrochloride, 0.67 part of an aqueous 10% sodium persulfate, 0.93 part of an aqueous 0.1% hydrogen peroxide, and 1.99 part of an aqueous 1% L-ascorbic acid solution. When the aqueous monomer solution was gelled about one minute after the introduction of the polymerization initiator, the stirring was discontinued and the aqueous monomer solution was left undergoing stationary polymerization. In about 40 minutes after the introduction of the polymerization initiator, the polymerization temperature reached its peak level of 54° C. After the peak, the reaction system was heated for 20 minutes in a hot water bath at 69° C. to terminate the polymerization. The resultant spongy gelled polymer absorbing water containing bubbles copiously was shredded with a cutter (produced by Asahi Sangyo K.K. and sold under the trademark of "Minislicer") and then dried in a hot air drier at 150° C. for 60 minutes. The dried polymer was pulverized with a desk-top pulverizer. The resultant powder was passed through a sieve with meshes of 850 μm. The particles which had passed the sieve were collected to furnish an absorbent cross-linked polymer (3), 310 μm in average particle diameter, of this invention containing —COOR groups in a concentration of 12.9 mmol/g and having a molecular ratio of —COOH/—COOR of 0.25 was obtained. The ratio of water absorption capacity, speed of absorption, content of water-soluble component, bulk specific gravity, and specific surface area of the absorbent cross-linked polymer (3) were 61.4 (g/g), 18 seconds, 8.8 wt %, 0.26 (g/ml), and 0.043 (m$^2$/g) respectively.

Referential Example 4

An aqueous monomer solution containing 42 parts of lithium hydroxide monohydrate, 96 parts of acrylic acid, 0.389 part of polyethylene glycol (n=8) diacrylate, 0.012 part of polyoxyethylene sorbitan monostearate (produced by Kao Corporation and sold under the trademark of "Leodol Super TW-S120"), and 268 parts of purified water was prepared. The aqueous monomer solution was deaerated with nitrogen, cooled to 24° C., and quickly stirred so that it stably yielded as dispersed bubbles of nitrogen gas therein and increased the volume thereof to 1.07 times the volume it had assumed before the dispersion of the bubbles and meanwhile made to add 1.33 parts of an aqueous 10% sodium persulfate solution and 0.67 part of an aqueous 1% L-ascorbic acid solution. When the aqueous monomer solution was gelled about two minutes after the introduction of the polymerization initiator, the stirring was discontinued and the aqueous monomer solution was left undergoing stationary polymerization. In about 45 minutes after the introduction of the polymerization initiator, the polymerization temperature reached its peak level of 73° C. After the peak, the reaction system was heated for 30 minutes in a hot water bath at 80° C. to terminate the polymerization. The resultant sponge of gel absorbing water polymer containing bubbles copiously was cut with scissors into cubes of about 20 mm and the porous cubes were subsequently dried in a hot air drier at 160° C. for 60 minutes. The dried cubes were pulverized with a desk-top pulverizer. The resultant powder was passed through a sieve with meshes of 850 μm. The particles which had passed the sieve were collected to furnish an absorbent cross-linked polymer (4), 310 μm in average particle diameter, of this invention containing —COOR groups in a concentration of 12.9 mmol/g and having a molecular ratio of —COOH/—COOR of 0.25 was obtained. The ratio of water absorption capacity, speed of absorption, content of water-soluble component, bulk specific gravity, and specific surface area of the absorbent cross-linked polymer (4) were 62.1 (g/g), 13 seconds, 14.4 wt %, 0.098 (g/ml), and 0.1615 (m$^2$/g) respectively.

Referential Example 5

An aqueous monomer solution containing 42 parts of lithium hydroxide monohydrate, 96 parts of acrylic acid, 0.389 part of polyethylene glycol (n=8) diacrylate, and 268 parts of purified water was prepared. The aqueous monomer solution was deaerated with nitrogen, cooled to 24° C., and quickly stirred under a stream of nitrogen so that it stably yielded as dispersed bubbles of nitrogen gas therein and increased the volume thereof to 1.03 times the volume it had assumed before the dispersion of the bubbles and meanwhile made to add 1.33 parts of an aqueous 10% sodium persulfate solution and 0.67 part of an aqueous 1% L-ascorbic acid solution. When the aqueous monomer solution was gelled about two minutes after the introduction of the polymerization initiator, the stirring was discontinued and the aqueous monomer solution was left undergoing stationary polymerization. In about 40 minutes after the introduction of the polymerization initiator, the polymerization temperature reached its peak level of 75° C. After the peak, the reaction system was heated for 30 minutes in a hot water bath at 80° C. to terminate the polymerization. The resultant sponge of gel absorbing water polymer containing bubbles copiously was cut with scissors into cubes of about 5 mm and the porous cubes were subsequently dried in a hot air drier at 160° C. for 120 minutes. The dried cubes were pulverized with a desk-top pulverizer. The resultant powder was passed through a sieve with meshes of 850 μm. The particles which had passed the sieve were collected to furnish an absorbent cross-linked polymer (5), 390 μm in average particle diameter, of this invention containing —COOR groups in a concentration of 12.9 mmol/g and having a molecular ratio of —COOH—COOR of 0.25 was obtained. The ratio of water absorption capacity, speed of absorption, content of water-soluble component, bulk specific gravity, and specific surface area of the absorbent cross-linked polymer (5) were 57.1 (g/g), 21 seconds, 13.5 wt %, 0.296 (g/ml), and 0.0371 (m$^2$/g) respectively.

Referential Example 6

A partially neutralized aqueous lithium acrylate solution obtained by uniformly mixing 45.21 parts of acrylic acid, 495.69 parts of an aqueous 30 wt % lithium acrylate solution, 0.3095 part (0.08 mol % based on monomer) of N,N'-methylene bisacrylamide as a cross-linking agent, and 254.42 parts of deionized water was placed in a cylindrical container and deaerated with nitrogen gas. Next, the partially neutralized aqueous lithium acrylate solution was kept at 14° C. and stirred with 2.5 parts of an aqueous 10 wt % 2,2'-azobis(2-amidinopropane) dihydrochloride (produced by Wako Pure Chemical Industries, Ltd. and sold under the trademark of "V-50 ") solution, 1.25 parts of an aqueous 10 wt % sodium persulfate solution, 1.1 parts of an aqueous 0.35 wt % hydrogen peroxide solution, and 1.76 parts of an aqueous 0.1 wt % L-ascorbic acid solution added thereto. In about one minute thence, the reaction system started polymerizing. The ensuant stationary adiabatic polymerization was continued for 1.5 hours. Then, the gel absorbing water polymer consequently obtained was extracted from the reaction vessel, placed in a kneader attached a jacket at 70° C., and stirred with blades for 15 minutes to shred the gel absorbing water into fragments, about 1–5 mm in diameter, and dried in a hot air drier at 160° C. for one hour. The dried fragments were pulverized with a desk-top pulverizer and passed a JIS standard sieve. From the resultant powder, the portion consisting of particles measuring 600–300 μm was separated to furnish an absorbent cross-linked polymer (6) containing —COOR groups in a concentration of 13.1 mmol/g and having a molecular ratio of —COOH/—COOR of 0.25 was obtained. The absorbent cross-linked polymer (6) thus obtained was found to have a ratio of water absorption capacity of 71.2 (g/g) and a content of water-soluble component of 18.2 wt %.

Referential Example 7

An aqueous acrylic acid solution obtained by uniformly mixing 160.00 parts of acrylic acid, 622.5 parts of deionized water, and 0.342 parts of N,N'-methylene bisacrylamide was placed in a cylindrical container and deaerated with nitrogen gas. Next, the aqueous acrylic acid solution was kept at 15° C. and stirred with 9.60 parts of an aqueous 5 wt % 2,2 1-azobis (2-amidinopropane) dichloride (produced by Wako Pure Chemical Industries, Ltd. and sold under the trademark of "V-50") solution, 4.57 parts of an aqueous 3.5 wt % hydrogen peroxide solution, and 4.00 parts of an aqueous 1 wt % L-ascorbic acid as a polymerization initiator added thereto. In about one minute thence, the reaction system started polymerizing. The ensuant stationary adiabatic polymerization was continued for 1.5 hours. Then, the gel absorbing water polymer consequently obtained was extracted from the reaction vessel, placed in a kneader attached a jacket at 70° C., and stirred with blades for 20 minutes to shred the gel absorbing water into fragments, about 1–5 mm in diameter. The fragments were treated with 1144.9 parts of an aqueous 3.48% lithium hydroxide solution to neutralize uniformly the carboxyl groups in the gel absorbing water until the color of phenolphthalein used as an indicator completely vanished. The neutralized gel absorbing water was dried in a hot air drier at 160° C. for one hour and pulverized with a desk-top pulverizer. The resultant powder was passed through a JIS standard sieve. From the produced powder, a portion consisting of particles 600–300 μm in particle diameter was separated to furnish an absorbent cross-linked polymer (7) containing —COOR groups in a concentration of 12.9 mmol/g and having a molecular ratio of —COOH/—COOR of 0.25 was obtained. The absorbent cross-linked polymer (7) thus obtained was found to have a ratio of water absorption capacity of 75.0 (g/g) and a content of water-soluble component of 9.1 wt %.

Referential Example 8

An aqueous monomer solution containing 42 parts of lithium hydroxide monohydrate, 96 parts of acrylic acid, 0.389 part of polyethylene glycol (n=8) diacrylate, and 268 parts of purified water was prepared. The aqueous monomer solution was deaerated with nitrogen, cooled to 24° C., and quickly stirred under a stream of nitrogen so that it stably yielded as dispersed bubbles of nitrogen gas therein and increased the volume thereof to 1.05 times the volume it had assumed before the dispersion of the bubbles and meanwhile made to add 1.33 parts of an aqueous 10% sodium persulfate solution and 0.67 part of an aqueous 1% L-ascorbic acid solution. When the aqueous monomer solution was gelled about two minutes after the introduction of the polymerization initiator, the stirring was discontinued and the aqueous monomer solution was left undergoing stationary polymerization. In about 33 minutes after the introduction of the polymerization initiator, the polymerization temperature reached its peak level of 70° C. After the peak, the reaction system was heated for 30 minutes in a hot water bath at 80° C. to terminate the polymerization. The resultant sponge of gel absorbing water polymer containing bubbles copiously was cut with scissors into cubes of about 5 mm and the porous cubes were subsequently dried in a hot air drier at 160° C. for 120 minutes. The dried cubes were pulverized with a desk-top pulverizer. The resultant powder was passed through a sieve with meshes of 850 μm. The particles which had passed the sieve were collected to furnish an absorbent cross-linked polymer (8), 350 μm in average particle diameter, of this invention containing —COOR groups in a concentration of 12.9 mmol/g and having a molecular ratio of —COOH/—COOR of 0.25 was obtained. The ratio of water absorption capacity, speed of absorption, content of water-soluble component, bulk specific gravity, and specific surface area of the absorbent cross-linked polymer (8) were 59.4 (g/g), 16 seconds, 14.0 wt %, 0.198 (g/ml), and 0.0509 ($m^2$/g) respectively.

Example 1

An aqueous liquid comprising a compound having a plurality of functional groups capable of reacting with —COOR groups, which composed of 0.03 part of ethylene glycol diglycidyl ether, 1 part of propylene glycol, 3 parts of purified water, and 2 parts of isopropanol was added to one hundred (100) parts of the absorbent cross-linked polymer (1), mixed and heated at 150° C. for 10 minutes to obtain an absorbent resin (1) of this invention having the proximity of the surface thereof yielded to a cross-linking treatment.

The speed of absorption, ratio of water absorption capacity, content of water-soluble component, ratio of water absorption capacity under pressure (50 g/$cm^2$), ratio of water absorption capacity under high pressure (100 g/$cm^2$), and ratio of water absorption capacity after five minutes' application of pressure of the absorbent resin (1) of this invention were 15 seconds, 42.2 (g/g), 15.0 wt %, 43.2 (g/g), 31.6 (g/g), and 29.9 (g/g) respectively. These results and BET specific surface area and Fine powder content were shown in Table 1.

Example 2

An aqueous liquid comprising a compound having a plurality of functional groups capable of reacting with —COOR groups, which composed of 0.25 part of ethylene glycol diglycidyl ether, 2.5 parts of propylene glycol, 7.5 parts of purified water, and 7.5 parts of isopropanol was added to one hundred (100) parts of the absorbent cross-linked polymer (2), and mixed and heated at 150° C. for 10 minutes to obtain an absorbent resin (2) of this invention having the proximity of the surface thereof yielded to a cross-linking treatment.

The speed of absorption, ratio of water absorption capacity, content of water-soluble component, ratio of water absorption capacity under pressure (50 g/cm$^2$), ratio of water absorption capacity under high pressure (100 g/cm$^2$), and ratio of water absorption capacity after five minutes' application of pressure of the absorbent resin (2) were 6 seconds, 36.0 (g/g), 8.2 wt %, 34.9 (g/g), 28.5 (g/g), and 31.1 (g/g) respectively.

Example 3

An aqueous liquid comprising a compound having a plurality of functional groups capable of reacting with —COOR groups, which composed of 0.3 part of ethylene glycol diglycidyl ether, 3 parts of propylene glycol, 9 parts of purified water, and 9 parts of isopropanol was added to one hundred (100) of the absorbent cross-linked polymer (3), and mixed and heated at 150° C. for 10 minutes to obtain an absorbent resin (3) of this invention having the proximity of the surface thereof yielded to a cross-linking treatment.

The speed of absorption, ratio of water absorption capacity, content of water-soluble component, ratio of water absorption capacity under pressure (50 g/cm$^2$), ratio of water absorption capacity under high pressure (100 g/cm$^2$), and ratio of water absorption capacity after five minutes' application of pressure of the absorbent resin (3) of this invention were 11 seconds, 40.0 (g/g), 7.9wt %, 38.5 (g/g), 29.4 (g/g), and 33.3 (g/g) respectively.

Example 4

An aqueous liquid comprising a compound having a plurality of functional groups capable of reacting with —COOR groups, which composed of 0.3 part of ethylene glycol diglycidyl ether, 3 parts of propylene glycol, 9 parts of purified water, and 9 parts of isopropanol was added to one hundred (100) part of the absorbent cross-linked polymer (3) and mixed and heated at 185° C. for 5 minutes to obtain an absorbent resin (4) of this invention having the proximity of the surface thereof yielded to a cross-linking treatment.

The speed of absorption, ratio of water absorption capacity, content of water-soluble component, ratio of water absorption capacity under pressure (50 g/cm$^2$), ratio of water absorption capacity under high pressure (100 g/cm$^2$), and ratio of water absorption capacity after five minutes, application of pressure of the absorbent resin (4) of this invention were 12 seconds, 41.2 (g/g), 7.2wt %, 39.3 (g/g), 30.1 (g/g), and 30.0 (g/g) respectively.

Example 5

An aqueous liquid comprising a compound having a plurality of functional groups capable of reacting with —COOR groups, which composed of 0.4 part of ethylene glycol diglycidyl ether, 4 parts of propylene glycol, 12 parts of purified water, and 12 parts of isopropanol was added to one hundred (100) parts of the absorbent cross-linked polymer (4) at 150° C. for 5 minutes to obtain an absorbent resin (5) of this invention having the proximity of the surface thereof yielded to a cross-linking treatment.

The speed of absorption, ratio of water absorption capacity, content of water-soluble component, ratio of water absorption capacity under pressure (50 g/cm$^2$), ratio of water absorption capacity under high pressure (100 g/cm$^2$), and ratio of water absorption capacity after five minutes, application of pressure of the absorbent resin (5) of this invention were 6 seconds, 38.3 (g/g), 13.4 wt %, 35.0 (g/g), 26.9 (g/g), and 31.0 (g/g) respectively.

Example 6

An aqueous liquid comprising a compound having a plurality of functional groups capable of reacting with —COOR groups, which composed of 0.3 part of ethylene glycol diglycidyl ether, 3 parts of propylene glycol, 9 parts of purified water, and 9 parts of isopropanol was added to one hundred (100) parts of the absorbent cross-linked polymer (5), and mixed and heated at 150° C. for 5 minutes to obtain an absorbent resin (6) of this invention having the proximity of the surface thereof yielded to a cross-linking treatment.

The speed of absorption, ratio of water absorption capacity, content of water-soluble component, ratio of water absorption capacity under pressure (50 g/cm$^2$), ratio of water absorption capacity under high pressure (100 g/cm$^2$), and ratio of water absorption capacity after five minutes' application of pressure of the absorbent resin (6) of this invention were 14 seconds, 40.0 (g/g), 12.5 wt %, 35.0 (g/g), 26.0 (g/g), and 25.7 (g/g) respectively.

Example 7

An aqueous liquid comprising a compound having a plurality of functional groups capable of reacting with —COOR groups, which composed of 0.05 part of ethylene glycol diglycidyl ether, 1 part of propylene glycol, 3 parts of purified water, and 3 parts of isopropanol was added to one hundred (100) parts of the absorbent cross-linked polymer (6), and mixed and heated at 185° C. for 10 minutes to obtain an absorbent resin (7) of this invention having the proximity of the surface thereof yielded to a cross-linking treatment.

The speed of absorption, ratio of water absorption capacity, content of water-soluble component, ratio of water absorption capacity under pressure (50 g/cm$^2$), ratio of water absorption capacity under high pressure (100 g/cm$^2$), and ratio of water absorption capacity after five minutes, application of pressure of the absorbent resin (7) of this invention were 42 seconds, 60.0 (g/g), 16.2 wt %, 38.5 (g/g), 28.1 (g/g), and 19.0 (g/g) respectively.

Example 8

An aqueous liquid comprising a compound having a plurality of functional groups capable of reacting with —COOR groups, which composed of 0.05 part of ethylene glycol diglycidyl ether, 1 part of propylene glycol, 3 parts of purified water, and 3 parts of isopropanol was added to one hundred (100) parts of the absorbent cross-linked polymer (7), mixed and heated at 185° C. for 60 minutes to obtain an absorbent resin (8) of this invention having the proximity of the surface thereof yielded to a cross-linking treatment.

The speed of absorption, ratio of water absorption capacity, content of water-soluble component, ratio of water absorption capacity under pressure (50 g/cm$^2$), ratio of water absorption capacity under high pressure (100 g/cm$^2$), and ratio of water absorption capacity after five minutes' application of pressure of the absorbent resin (8) of this invention were 44 seconds, 59.7 (g/g), 7.0wt %, 34.8 (g/g), 25.4 (g/g), and 16.0 (g/g) respectively.

Example 9

An aqueous liquid comprising a compound having a plurality of functional groups capable of reacting with —COOR groups, which composed of 0.3 part of ethylene glycol diglycidyl ether, 3 parts of propylene glycol, 9 parts of purified water, and 9 parts of isopropanol was added to one hundred (100) parts of the absorbent cross-linked polymer (8), mixed and heated at 150° C. for 10 minutes to obtain an absorbent resin (9) of this invention having the proximity of the surface thereof yielded to a cross-linking treatment.

The speed of absorption, ratio of water absorption capacity, content of water-soluble component, ratio of water absorption capacity under pressure (50 g/cm$^2$), ratio of water absorption capacity under high pressure (100 g/cm$^2$), and ratio of water absorption capacity after five minutes' application of pressure of the absorbent resin (9) of this invention were 10 seconds, 40.0 (g/g), 22.8 wt %, 30.0 (g/g), 0 (g/g), and 26.4 (g/g) respectively.

Control 1

An aqueous monomer solution containing 96.00 parts of acrylic acid, 65.24 parts of potassium hydroxide of a plurality of 86%, 0.5192 part of polyethylene glycol (n=8) diacrylate, and 397.06 parts of deionized water was prepared. The aqueous monomer solution was deaerated with nitrogen, cooled to 14° C., and quickly stirred under a stream of nitrogen so that it stably yielded as dispersed bubbles of nitrogen gas therein and increased the volume thereof to 1.02 times the volume it had assumed before the dispersion of the bubbles and meanwhile made to add 1.33 parts of an aqueous 10% 2,2'-azobis(2-amidinopropane) dihydrochloride (produced by Wako Pure Chemical Industries, Ltd. and sold under the trademark of "V-50") solution, 0.67 part of an aqueous 10 wt % sodium persulfate solution, 1.99 parts of an aqueous 0.1 wt % hydrogen peroxide solution, and 0.93 part of an aqueous 0.1 wt % L-ascorbic acid solution as a polymerization initiator. In about one minute, the reaction system started polymerizing. The ensuant stationary adiabatic polymerization was continued for 1.5 hours. The produced bubble-containing gel absorbing water polymer was extracted from the reaction vessel, shredded into fragments, about 1–5 mm in particle diameter, and then dried in a hot air drier at 160° C. for one hour. The dried fragments were pulverized with a desk-top pulverizer. The resultant powder was passed through a sieve with meshes of 850 μm. The particles which had passed the sieve were collected to furnish a porous absorbent cross-linked polymer (1) for comparison, 360 μm in average particle diameter, containing —COOR groups in a concentration of 9.82 mmol/g and having a molecular ratio of —COOH/—COOR of 0.25 was obtained. The ratio of water absorption capacity, speed of absorption, and content of water-soluble component of the absorbent cross-linked polymer (1) for comparison were 60.4 (g/g), 22 seconds, and 25.7 wt % respectively.

An aqueous liquid comprising a compound having plural of functional groups capable of reacting with —COOR groups, which composed of 0.3 part of ethylene glycol diglycidyl ether, 3 parts of propylene glycol, 9 parts of purified water, and 9 parts of isopropanol was added to one hundred (100) parts of the absorbent cross-linked polymer (1) for comparison, and mixed and 0.03 part of ethylene glycol diglycidyl ether, 1 part of propylene glycol, 3 parts of purified water, and 2 parts of isopropanol were added to one hundred (100) parts of the absorbent cross-linked polymer (1) for comparison, mixed and heated heated at 185° C. for 30 minutes to obtain an absorbent resin (1) for comparison having the proximity of the surface thereof yielded to a cross-linking treatment.

The speed of absorption, ratio of water absorption capacity, content of water-soluble component, ratio of water absorption capacity under pressure (50 g/cm$^2$), ratio of water absorption capacity under high pressure (100 g/cm$^2$), and ratio of water absorption capacity after five minutes' application of pressure of the absorbent resin (1) for comparison of this invention were 23 seconds, 40.0 (g/g), 24.0 wt %, 23.0 (g/g), 18.6 (g/g), and 10.0 (g/g) respectively.

Control 2

An aqueous monomer solution containing 96.00 parts of acrylic acid, 58.62 parts of an aqueous 29% ammonia solution, 0.5192 part of polyethylene glycol (n=8) diacrylate, and 193.58 parts of deionized water was prepared. The aqueous monomer solution was deaerated with nitrogen, cooled to 14° C., and quickly stirred under a stream of nitrogen so that it stably yielded as dispersed bubbles of nitrogen gas therein and increased the volume thereof to 1.02 times the volume it had assumed before the dispersion of the bubbles and meanwhile made to add 1.33 parts of an aqueous 10% 2,2'-azobis(2-amidinopropane) dihydrochloride (produced by Wako Pure Chemical Industries, Ltd. and sold under the trademark of "V-50") solution, 0.67 part of an aqueous 10 wt % sodium persulfate solution, 1.99 parts of an aqueous 0.1 wt % hydrogen peroxide solution, and 0.93 part of an aqueous 0.1 wt % L-ascorbic acid solution as a polymerization initiator. In about one minute, the reaction system started polymerizing. The ensuant stationary adiabatic polymerization was continued for 1.5 hours. The produced bubble-containing gel absorbing water polymer was extracted from the reaction vessel, shredded into fragments, about 1–5 mm in particle diameter, and then dried in a hot air drier at 150° C. for one hour. The dried fragments were pulverized with a desk-top pulverizer. The resultant powder was passed through a sieve with meshes of 850 μm. The particles which had passed the sieve were collected to furnish an porous absorbent cross-linked polymer (2) for comparison, 290 μm in average particle diameter, containing —COOR groups in a concentration of 11.7 mmol /g and having a molecular ratio of —COOH/—COOR of 0.25 was obtained. The ratio of water absorption capacity, speed of absorption, and content of water-soluble component of the absorbent cross-linked polymer (2) for comparison were 57.2 (g/g). 22 seconds, and 17.4 wt % respectively.

An aqueous liquid comprising a compound having a plurality of functional groups capable of reacting with —COOR groups, which composed of 0.03 part of ethylene glycol diglycidyl ether, 1 part of propylene glycol, 3 parts of purified water, and 2 parts of isopropanol was added to one hundred (100) parts of the absorbent cross-linked polymer (2) for comparison, and mixed and heated at 120° C. for 30 minutes to obtain an absorbent resin (2) for comparison having the proximity of the surface thereof yielded to a cross-linking treatment.

The speed of absorption, ratio of water absorption capacity, content of water-soluble component, ratio of water absorption capacity under pressure (50 g/cm$^2$), ratio of water absorption capacity under high pressure (100 g/cm$^2$), and ratio of water absorption capacity after five minutes' application of pressure of the absorbent resin (2) for comparison of this invention were 25 seconds, 37.2 (g/g), 17.1 wt %, 19.3 (g/g), 17.7 (g/g), and 11.3 (g/g) respectively.

Control 3

An aqueous monomer solution containing 40 parts of sodium hydroxide, 96 parts of acrylic acid, 0.5192 part of polyethylene glycol (n=8) diacrylate, 0.01 part of polyoxyethylene sorbitan monostearate (produced by Kao Corporation and sold under the trademark of "Leodol Super TW-S-120:), and 350 parts of purified water was prepared. The aqueous monomer solution was deaerated with nitrogen, cooled to 12° C., and quickly stirred so that it stably yielded as dispersed bubbles of nitrogen gas therein and increased the volume thereof to 1.04 times the volume it had assumed before the dispersion of the bubbles and meanwhile made to add 1.33 parts of an aqueous 10 wt % 2,2'-azobis(2-methyl-propionamidoine) dihydrochloride solution, 0.67 part of an aqueous 10 wt % sodium persulfate solution, 0.93 part of an aqueous 0.1% hydrogen peroxide solution, and 1.99 parts of an aqueous 0.1% L-ascorbic acid solution. When the aqueous monomer solution was gelled about two minutes after the introduction of the polymerization initiator, the stirring was discontinued and the aqueous monomer solution was left undergoing stationary polymerization. After the peak of the polymerization temperature, the reaction system was heated in a hot water bath at 69° C. for 20 minutes to terminate the polymerization. The resultant sponge of gel absorbing water polymer containing bubbles copiously was cut with scissors and then dried in a hot air drier at 150° C. for 60 minutes. The dried fragments were pulverized with a desk-top pulverizer. The resultant powder was passed through a sieve with meshes of 850 μm. The particles which had passed the sieve were collected to furnish an absorbent cross-linked polymer (3) for comparison, 290 min average particle diameter, containing —COOR groups in a concentration of 11.1 mmol/g and having a molecular ratio of —COOH/—COOR of 0.25 was obtained. The ratio of water absorption capacity, speed of absorption, content of water-soluble component, and bulk specific gravity of the absorbent cross-linked polymer (3) for comparison were 57.3 (g/g), 20 seconds, 19.6 wt %, and 0.27 (g/ml) respectively.

An aqueous liquid comprising a compound having a plurality of functional groups capable of reacting with —COOR groups, which composed 0.3 part of ethylene glycol diglycidyl ether, 3 parts of propylene glycol, 9 parts of purified water, and 9 parts of isopropanol was added to one hundred (100) parts of the absorbent cross-linked polymer (3) for comparison, mixed and heated at 185° C. for 30 minutes to obtain an absorbent resin (3) for comparison having the proximity of the surface thereof yielded to a cross-linking treatment.

The speed of absorption, ratio of water absorption capacity, content of water-soluble component, ratio of water absorption capacity under pressure (50 g/cm$^2$), ratio of water absorption capacity under high pressure (100 g/cm$^2$), and ratio of water absorption capacity after five minutes, application of pressure of the absorbent resin (3) for comparison of this invention were 19 seconds, 41.5 (g/g), 18.8 wt %, 28.0 (g/g), 19.8 (g/g), and 9.8 (g/g) respectively.

Control 4

A reaction vessel fabricated by fitting a lid to a jacketed twin-arm type kneader of stainless steel, 10 liters in inner volume, attached two sigma blades was charged with a reaction solution prepared by dissolving 4.73 g of polyethylene glycol (n=8) diacrylate as an inner cross-linking agent in 5367 g of an aqueous 33 wt % partially neutralized sodium acrylate solution having a ratio of neutralization of 75 mol %. Next, the air entrapped in the reaction vessel was displaced with nitrogen, with the temperature of the reaction solution kept at 26° C. Then, the reaction solution was kept stirred by the blades of the kneader and meanwhile made to add 12 g of an aqueous 20 wt % sodium persulfate solution as a polymerization initiator and 10 g of an aqueous 1 wt % L-ascorbic acid solution. The ensuant polymerization was continued as accompanied by disintegration of the formed gel for 60 minutes.

Thereafter, the resultant polymer was dried, pulverized, and classified with 850 μm sieve similarly in Example 1 to obtain an absorbent cross-linked polymer (4) for comparison. This polymer had a water content of 6 wt %. The ratio of water absorption capacity, speed of absorption, content of water-soluble component, and bulk specific gravity of the absorbent cross-linked polymer (4) for comparison were 51.3 (g/g), 20 seconds, 12.6 wt %, and 0.68 (g/ml) respectively.

Subsequently, an aqueous liquid comprising a compound having a plurality of functional groups capable of reacting with —COOR groups, which composed of 0.03 part of ethylene glycol diglycidyl ether, 1 part of propylene glycol, 3 parts of purified water, and 2 parts of isopropanol added to one hundred parts of the absorbent cross-linked polymer (4) for comparison, containing —COOR groups in a concentration of 11.4 mmol/g and having a molecular ratio of —COOH/—COOR of 0.25 was obtained, and mixed and heated at 185° C. for 40 minutes to obtain an absorbent resin (4) for comparison having the proximity of the surface thereof yielded to a cross-linking treatment.

The speed of absorption, ratio of water absorption capacity, content of water-soluble component, ratio of water absorption capacity under pressure (50 g/cm$^2$), ratio of water absorption capacity under high pressure (100 g/cm$^2$), and ratio of water absorption capacity after five minutes' application of pressure of the absorbent resin (4) for comparison were 40 seconds, 41.0 (g/g), 11.3 wt %, 34.0 (g/g), 17.4 (g/g), and 19.8 (g/g) respectively.

Control 5

An absorbent cross-linked polymer (5) for comparison was obtained by following the procedure of Control 4 while changing the concentration of 5367 g of the aqueous monomer solution used for polymerization to 38 wt % and using 2.51 g of trimethylol propane triacrylate instead as an inner cross-linking agent. This polymer had a water content of 6 wt %. The ratio of water absorption capacity, content of water-soluble component, and bulk specific gravity of the absorbent cross-linked polymer (5) for comparison were 44.0 (g/g), 12.5 wt %, and 0.69 (g/ml) respectively.

Subsequently, an aqueous liquid comprising a compound having a plurality of functional groups capable of reacting with —COOR groups, which composed of 0.5 part of glycerin, 2 parts of isopropanol, and 1 part of water was added to one hundred (100) parts of the absorbent cross-linked polymer (5) for comparison mixed and heated at 205° C. for 30 minutes to obtain an absorbent resin (5) for comparison having the proximity of the surface thereof yielded to a cross-linking treatment.

The speed of absorption, ratio of water absorption capacity, content of water-soluble component, ratio of water absorption capacity under pressure (50 g/cm$^2$), ratio of water absorption capacity under high pressure (100 g/cm$^2$), and ratio of water absorption capacity after five minutes' application of pressure of the absorbent resin (5) for comparison were 40 seconds, 36.0 (g/g), 11.9 wt %, 30.0 (g/g), 15.5 (g/g) and 17.8 (g/g) respectively.

Control 6

To cite an example of a commercially available absorbent resin manifesting a high ratio of water absorption capacity under pressure, a product of Chendal Corp (cross-linked sodium polyacrylate) sold under the trademark of "ASAP 2300" was used as an absorbent resin (6) for comparison.

The ratio of water absorption capacity, ratio of water absorption capacity, content of water-soluble component, ratio of water absorption capacity under pressure (50 g/cm$^2$), ratio of water absorption capacity under high pressure (100 g/cm$^2$), and ratio of water absorption capacity after five minutes' application of pressure of the absorbent resin (6) for comparison were 45 seconds, 38.7 g/g, 6.0 wt %, 32.0 g/g, 18.3 g/g, and 19.3 g/g respectively.

Example 10

By the use of a mixer, 50 parts by weight of the pressure-resistant absorbent resin (9) containing —COOR groups in a concentration of 12.0 mmol/g or more and having a molecular ratio of —COOH/—COOR of 0.25 obtained in Example 9and manifesting a ratio of water absorption capacity of 30.0 (g/g) under pressure of 50 g/cm$^2$ and a pressure-resistant absorption ratio of 0.76 and 50 parts by weight of wood-ground pulp were dry mixed. Then, the produced mixture was pneumatically deposited in the form of sheet on a wire screen with 400 meshes (mesh size 38 $\mu$m), by a batch type pneumatic sheet producing device to furnish a web measuring 120 mm×400 mm. An absorbent article having a basis weight of about 0.047 (g/cm$^2$) was obtained by pressing the web with a pressure of 2 (kg/cm$^2$) for five seconds.

Subsequently, a disposable diaper (1) using a pressure-resistant absorbent resin was obtained by superposing a back sheet (liquid-impervious sheet) made of liquid-impervious polypropylene and attached a so-called leg gather, the absorbent article mentioned above, and a top sheet (liquid-pervious sheet) made of liquid-pervious polypropylene in the order mentioned, joining them with two so-called tape fasteners and joining the superposed layers with a double-face adhesive tape and fitting two so-called tape fasteners to the superposed layers. This disposable diaper (1) weighed 46 g.

Control 7

An absorbent article for comparison was obtained by following the procedure of Example 10 while using an absorbent resin (5) for comparison obtained in Control 5, containing —COOR groups in a concentration of not more than 12 mmol/g and having a molecular ratio of —COOH/—COOR of 0.25, and having the same ratio of water absorption capacity under pressure (30 g/g) as the absorbent resin (10), and manifesting a pressure-resistant ratio of 0.51 in the place of the absorbent resin (10) obtained in Example 9 and manifesting a pressure-resistant ratio of 0.76. Weight of the absorbent article (1) for comparison is 46 g.

Example 11

The disposable diaper (1) using the absorbent resin (9) obtained in Example 11 and manifesting a ratio of water absorption capacity under pressure of 30 g/g and a pressure-resistant ratio of 0.76 and the disposable diaper (1) for comparison using the pressure-resistant absorbent resin (9) obtained in Control 7 and manifesting a ratio of water absorption capacity under pressure of 30 g/g and a pressure-resistant absorption ratio of 0.52 were subjected to one week's monitor test performed on babies of employees of Nippon Shokubai Co. LTD. The results indicate that the disposable diaper (1) using the pressure-resistant absorbent resin excelled in springness of leak and amount of urine absorbed. It was demonstrated that with the same ratio of water absorption capacity under pressure (30 g/g), the absorbent resin of a low pressure-resistant absorption ratio (0.76 vs 0.52) failed to furnish a fully satisfactory disposable diaper.

Example 12

Ratio of water absorption capacity under pressure and under high pressure

By the use of a mixer, 50 parts by weight of the pressure-resistant absorbent resin and 50 parts by weight of wood-ground pulp were dry mixed. Then, the produced mixture was pneumatically deposited in the form of sheet on a wire screen with 400 meshes (mesh size 38 $\mu$m), by a batch type pneumatic sheet producing device to furnish a web measuring 120 mm×400 mm. An absorbent article having a basis weight of about 0.047 (g/cm$^2$) was obtained by pressing the web with a pressure of 2 (kg/cm$^2$) for five seconds. Sample for evaluation of disposable diaper produced by cutting the absorbent article with a round shape in diameter of 60 mm and forming. Ratio of water absorption capacity under pressure and under high pressure of the absorbent article were measured using the sample for determination.

The determination of the ratio of water absorption capacity under high pressure of the absorbent article used a measuring device of mentioned above and determined as same, besides using sample for evaluation on a supporting cylinder 8.

Ratio of water absorption capacity under pressure (50 g/cm$^2$) and a ratio of water absorption capacity under high pressure (100 g/cm$^2$) of the absorbent article was computed in accordance with the following formula a using weight of artificial urine 11($W_3$ g) for 60 minutes form start of absorption of artificial urine.

Formula d: Ratio of water absorption capacity under pressure and of ratio of water absorption capacity under high pressure of absorbent article (g/g)=weight of artificial urine ($W_3$ g)/weight of sample for evaluation($W_4$ g) A ratio of water absorption capacity under pressure and a ratio of water absorption capacity under high pressure of an absorbent article using absorbent cross-linked polymer obtained example 1–8, having —COOR group of 12 mmol/g or more and a molecular ratio of —COOH/—COOR being 0.5 were determined. The result shows FIG. 1.

Control 8

A ratio of water absorption capacity under pressure and a ratio of water absorption capacity under high pressure of an absorbent article for diaper using absorbent cross-linked polymer obtained control 1–5, having—COOR group of not more than 12 mmol/g and a molecular ratio of —COOH/—COOR being 0.25 were determined instead of using absorbent cross-linked polymer obtained example 12 of absorbent article for diaper, having —COOR group of 12 mmol/g or more and a molecular ratio of —COOH/—COOR being 0.25. These results was shown in Table 2.

The entire disclosure of Japanese Patent Application No.9-96067 filed on Apr. 14, 1997, and Japanese Patent Application No.9-156267 filed on Jun. 13, 1997 including specification, claims, drawing and summary are incorporated herein by reference in its entirety.

TABLE 1

| number | Example | | | | | | | | |
|---|---|---|---|---|---|---|---|---|---|
| | 1 | 2 | 3 | 4 | 5 | 6 | 7 | 8 | 9 |
| Speed of absorption | 15 | 6 | 11 | 12 | 6 | 14 | 42 | 44 | 10 |
| Ratio of water absorption capacity (g/g) | 42.2 | 36.0 | 40.0 | 41.2 | 38.3 | 40.0 | 60.0 | 59.7 | 40.0 |
| content of water-soluble component (wt %) | 15.0 | 8.2 | 7.9 | 7.2 | 13.4 | 12.5 | 16.2 | 7.0 | 22.8 |
| Ratio of water absorption capacity under pressure (50 g/cm$^2$) (g/g) | 43.2 | 34.9 | 38.5 | 39.3 | 35.0 | 35.0 | 38.5 | 34.8 | 30.0 |
| Ratio of water absorption capacity under high pressure (100 g/cm$^2$) (g/g) | 31.6 | 28.5 | 29.4 | 30.1 | 26.9 | 26.0 | 28.1 | 25.4 | 23.0 |
| Pressure-resistant absorption ratio | 0.73 | 0.82 | 0.76 | 0.77 | 0.77 | 0.74 | 0.73 | 0.73 | 0.76 |
| Ratio of water absorption capacity after 5 minutes | 29.9 | 31.1 | 33.3 | 30.0 | 31.0 | 25.7 | 19.0 | 16.0 | 26.4 |
| BET specific surface area | 0.034 | 0.105 | 0.035 | 0.034 | 0.091 | 0.030 | 0.010 | 0.009 | 0.041 |
| Fine powder content (wt %) | 20 | 7 | 6 | 7 | 5 | 7 | 0 | 0 | 6 |

| number | Control | | | | | |
|---|---|---|---|---|---|---|
| | 1 | 2 | 3 | 4 | 5 | 6 |
| Speed of absorption | 23 | 25 | 19 | 40 | 40 | 45 |
| Ratio of water absorption capacity (g/g) | 40.0 | 37.2 | 41.5 | 41.0 | 36.0 | 38.7 |
| content of water-soluble component (wt %) | 24.0 | 17.1 | 18.8 | 11.3 | 11.9 | 6.0 |
| Ratio of water absorption capacity under pressure (50 g/cm$^2$) (g/g) | 23.0 | 19.3 | 28.0 | 34.0 | 30.0 | 32.0 |
| Ratio of water absorption capacity under high pressure (100 g/cm$^2$) (g/g) | 18.6 | 17.7 | 19.8 | 17.4 | 15.5 | 18.3 |
| Pressure-resistant absorption ratio | 0.81 | 0.92 | 0.71 | 0.51 | 0.52 | 0.57 |
| Ratio of water absorption capacity after 5 minutes | 10.0 | 11.3 | 9.8 | 19.8 | 17.8 | 19.3 |
| BET specific surface area | 0.024 | 0.022 | 0.028 | 0.010 | 0.009 | 0.025 |
| Fine powder content (wt %) | 6 | 6 | 7 | 0 | 0 | 1> |

TABLE 2

| | Ratio of water absorption capacity under high pressure (50 g/cm$^2$) for diaper (g/g) | Ratio of water absorption capacity high under pressure (100 g/cm$^2$) for diaper (g/g) |
|---|---|---|
| Absorbent resin of Example (1) | 23.6 | 19.7 |
| Absorbent resin of Example (2) | 18.9 | 17.8 |
| Absorbent resin of Example (3) | 21.0 | 18.4 |
| Absorbent resin of Example (4) | 21.4 | 18.8 |
| Absorbent resin of Example (5) | 19.0 | 16.9 |
| Absorbent resin of Example (6) | 19.3 | 16.5 |
| Absorbent resin of Example (7) | 21.0 | 17.6 |
| Absorbent resin of Example (8) | 18.9 | 16.0 |
| Absorbent resin of Example (1) | 12.1 | 12.0 |
| Absorbent resin of Control (2) | 10.0 | 11.4 |
| Absorbent resin of Control (3) | 15.0 | 12.7 |
| Absorbent resin of Control (4) | 17.9 | 11.3 |
| Absorbent resin of Control (5) | 16.0 | 10.0 |

What is claimed is:

1. A disposable diaper using a pressure-resistant absorbent resin manifesting a ratio of water absorption capacity under pressure of 30 g/g or more to artificial urine under a load of 50 g/cm$^2$, and a pressure-resistant absorption ratio of 0.6 or more, wherein said pressure-resistant absorption ratio is defined as the ratio of said ratio of water absorption capacity under high pressure to artificial urine under a load of 100 g/cm$^2$ to a ratio of water absorption capacity under pressure to artificial urine under a load of 50 g/cm$^2$.

2. An absorbent resin produced by adding a compound having a plurality of functional groups capable of reacting with a group represented by formula —COOR in which each R is independently hydrogen atoms, metal atoms or ammonium to an absorbent cross-linked polymer having a —COOR group of 12 mmol/g or more and a molecular ratio of —COOH/—COOR of not more than 0.5.

3. The absorbent resin according to claim 2, wherein said absorbent cross-linked polymer is at least one polymer selected from the group of cross-linked lithium polymaleate, cross-linked sodium polymaleate, cross-linked lithium polyfumarate, cross-linked sodium polyfumarate, cross-linked lithium polyitaconate, cross-linked lithium polymesaconate, cross-linked lithium polycitraconate, cross-linked lithium polyacrylate having a degree of neutralization in the range of 500–100 mol % respectively, cross-linked sodium polyitaconate, cross-linked sodium polymesaconate and cross-linked sodium polycitraconate having a degree of neutralization in the range of 50–83.2 mol % respectively.

4. The absorbent resin according to claim 3, wherein said absorbent cross-linked polymer is cross-linked lithium polyacrylate having a degree of neutralization in the range of 50–100 mol %.

5. The absorbent resin according to claim 2, wherein said absorbent cross-linked polymer is subjected to a surface cross-linking treatment with a first surface cross-linking agent having a solubility parameter of not less than 12.5 $(cal/cm^3)^{1/2}$ and a second surface cross-linking agent having the solubility parameter of not more than 12.5 $(cal/cm^3)^{1/2}$.

6. The absorbent resin according to claim 5, wherein said absorbent cross-linked polymer is heated at the temperature of 80–220° C. after addition of said surface cross-linking agent and said second surface cross-linking agent.

7. The absorbent resin according to claim 2, wherein said absorbent cross-linked polymer is obtainable by any one of (a)–(d) methods:
  (a) a method which polymerizes an aqueous lithium acrylate solution containing a copolymerizing cross-linking monomer and having a degree of neutralization in the range of 50–100 mol % in the presence of a polymerization initiator in a state having bubbles of inert gas dispersed;
  (b) a method which polymerized an aqueous lithium acrylate solution containing a copolymerizing cross-linking monomer and having a degree of neutralization in the range of 50–100 mol % in the presence of a polymerization initiator and surfactant in a state having bubbles of inert gas dispersed;
  (c) a method which subjects an aqueous lithium acrylate solution containing a copolymerizing cross-linking monomer and having a degree of neutralization in the range of 50–100 mol % to reversed-phase suspension polymerization in an organic solvent in the presence of a polymerization initiator and a surfactant;
  (d) a method which polymerizes an aqueous acrylic acid solution containing a copolymerizing cross-linking monomer in the presence of a polymerization initiator and, subsequent to the polymerization, adds an aqueous solution of lithium carbonate or lithium hydroxide to the resultant polymerization product to neutralize 50–100 mol % of the acid bases.

8. An absorbent resin having the proximity of the surface thereof subjected to a cross-linking treatment with a compound having plural of functional groups capable of reacting with a group represented by formula —COOR in which each R is independently hydrogen atoms, metal atoms or ammonium, having a —COOR group in a concentration of 12 mmol/g or more and a molecular ratio of —COOH/—COOR of not more than 0.5.

9. An absorbent resin having a BET specific surface area of 0.03 $m^2/g$ or more and a ratio of water absorption capacity under high pressure of 25 g/g or more to artificial urine under a load of 100 $g/cm^2$.

10. The absorbent resin according to claim 9, which is produced by adding a compound having a plurality of functional groups capable of reacting with a group represented by formula —COOR in which each R is independently hydrogen atoms, metal atoms or ammonium to an absorbent cross-linked polymer having a —COOR group 12 mmol/g or more and a molecular ratio of —COOH/—COOR of not more than 0.5.

11. The absorbent resin according to claim 9 or 10, which contains fine powder having a particle diameter of 150 μm or less in a concentration of 10 wt % or less.

12. The absorbent resin according to claim 9, wherein said ratio of water absorption capacity under high pressure is 28 g/g or more.

13. The absorbent resin according to claim 9, wherein said ratio of water absorption capacity under high pressure is 30 g/g or more.

14. The absorbent resin according to claim 9, comprising fine powder of a particle diameter of 150 μm or less in the range of not more than 20 wt %.

15. A pressure-resistant absorbent resin manifesting a ratio of water absorption capacity under pressure of 30 g/g or more to artificial urine under a load of 50 $g/cm^2$, and a pressure-resistant absorption ratio of 0.6 or more, wherein said pressure-resistant absorption ratio is defined as the ratio of said ratio of water absorption capacity under high pressure to artificial urine under a load of 100 $g/cm^2$ to a ratio of water absorption capacity under pressure to artificial urine under a load of 50 $g/cm^2$.

16. The pressure-resistant absorbent resin according to claim 15, further manifesting a ratio of water absorption capacity of 35 g/g or more to artificial urine under no load.

17. The pressure-resistant absorbent resin according to claim 15, wherein said ratio of water absorption capacity to artificial urine under a pressure load of 50 $g/cm^2$ is 33 g/g or more.

18. The pressure-resistant absorbent resin according to claim 15, further manifesting a ratio of water absorption capacity of 22 g/g or more to artificial urine under a high pressure load of 100 $g/cm^2$.

19. The pressure-resistant absorbent resin according to claim 15, comprising a water-soluble component in a concentration of not more than 15 wt %.

20. The pressure-resistant absorbent resin according to claim 15, wherein said pressure-resistant absorption ratio is 0.75 or more.

21. The pressure-resistant absorbent resin according to claim 15, which is obtainable by adding a compound having a plurality of functional groups capable of reacting with a group represented by formula —COOR in which each R is independently hydrogen atoms, metal atoms or ammonium to an absorbent cross-linked polymer having a —COOR group of 12 mmol/g or more and a molecular ratio of —COOH/—COOR of not more than 0.5 and heating the resultant mixture.

22. The pressure-resistant absorbent resin according to claim 21, wherein said compound is a covalent bond-forming cross-linking agent and said covalent bond-forming cross-linking agent serves for lowering the ratio of water absorption capacity of said absorbent cross-linked polymer under no load to 0.9–0.3 times the level which existed prior to cross-linking.

23. The disposable diaper using any one of said pressure-resistant absorbent resins according to claim 16–22.

24. The disposable diaper according to claim 13, which comprising of a core concentration of 30–100% defined as the absorbent resin to fiber material and absorbent resin.

25. A method for the production of an absorbent resin, characterized by adding a compound having a plurality of functional groups capable of reacting with a group represented by formula —COOR in which each R is independently hydrogen atoms, metal atoms or ammonium to an absorbent cross-linked polymer having a —COOR group of 12 mmol/g or more and a molecular ratio of —COOH/—COOR of not more than 0.5 and heating the resultant mixture.

26. The method according to claim 25, wherein said compound is a covalent bond-forming cross-linking agent and said covalent bond-forming cross-linking agent serves the purpose of lowering the ratio of water absorption capacity of said absorbent cross-linked polymer under no load to 0.9–0.3 times the level which existed prior to cross-linking.

* * * * *